(12) United States Patent
Yasumura et al.

(10) Patent No.: US 7,901,858 B2
(45) Date of Patent: Mar. 8, 2011

(54) MIXED CYCLIC PHENOL SULFIDES, AND CHARGE CONTROL AGENTS AND TONERS USING THE SAME

(75) Inventors: Masateru Yasumura, Ibaraki (JP); Masami Ito, Fukushima (JP); Naohiro Tarumoto, Tokyo (JP); Yoshikazu Aoki, Fukushima (JP); Masafumi Umekawa, Fukushima (JP); Masaki Okubo, Fukushima (JP); Hideyuki Otsuka, Fukushima (JP); Jun Watanabe, Fukushima (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/240,520

(22) Filed: Sep. 29, 2008

(65) Prior Publication Data

US 2009/0035678 A1 Feb. 5, 2009

Related U.S. Application Data

(63) Continuation of application No. PCT/JP2007/056576, filed on Mar. 28, 2007.

(30) Foreign Application Priority Data

Mar. 29, 2006 (JP) .................................. 2006-090976

(51) Int. Cl.
G03G 9/097 (2006.01)
(52) U.S. Cl. ...................................................... 430/108.5
(58) Field of Classification Search ............... 430/108.5; 549/11
See application file for complete search history.

(56) References Cited

U.S. PATENT DOCUMENTS

| | | | |
|---|---|---|---|
| 4,338,390 | A | 7/1982 | Lu |
| 4,391,890 | A | 7/1983 | Lu |
| 4,394,430 | A | 7/1983 | Jadwin et al. |
| 4,767,688 | A | 8/1988 | Hashimoto et al. |
| 5,049,467 | A | 9/1991 | Yamanaka |
| 5,824,808 | A | 10/1998 | Hori et al. |
| 2003/0017407 | A1 | 1/2003 | Nakamura et al. |
| 2009/0264661 | A1* | 10/2009 | Yasumura et al. ............ 549/9 |

FOREIGN PATENT DOCUMENTS

| | | |
|---|---|---|
| DE | 101 41 A1 | 11/2002 |
| JP | 55-42752 B | 11/1980 |
| JP | 57-111541 A | 7/1982 |
| JP | 57-119364 A | 7/1982 |
| JP | 58-9154 A | 1/1983 |
| JP | 58-98742 A | 6/1983 |
| JP | 61-3149 A | 1/1986 |
| JP | 61-69073 B | 4/1986 |
| JP | 61-141453 A | 6/1986 |
| JP | 61-221756 A | 10/1986 |
| JP | 62-94856 A | 5/1987 |
| JP | 1-306861 A | 12/1989 |
| JP | 2-201378 A | 8/1990 |
| JP | 7-64336 A | 3/1995 |
| JP | 2568675 B | 10/1996 |
| JP | 9-227553 A | 9/1997 |
| JP | 10-81680 A | 3/1998 |
| JP | 10-81681 A | 3/1998 |
| JP | 11-49770 A | 2/1999 |
| JP | 2899038 B | 3/1999 |
| JP | 3313871 B | 5/2002 |
| JP | 2002-207272 A | 7/2002 |
| JP | 3325730 B | 7/2002 |
| JP | 2002-255961 A | 9/2002 |
| JP | 2002-296845 A | 10/2002 |
| JP | 3359657 B | 10/2002 |
| JP | 2003-162100 A | 6/2003 |
| JP | 2003-241334 A | 8/2003 |
| JP | 2003-295522 A | 10/2003 |
| WO | WO 2008/026636 A1 * | 3/2008 |

OTHER PUBLICATIONS

Kon N., et.al.,"Synthesis of p-tert-butylthiacalix[n]arenes (n=4,6, and 8) from a sulfur-bridged acyclic dimer of p-tert-butylphenol," Tetrahedron Letters, vol. 43 (2002), pp. 2231-2234.*
Japanese Patent Office machine-assisted translation of JP 2003-295522 (pub. Oct. 2003).*
American Chemical Society (ACS) abstract AN 2008:285727, describing WO-2008/026636 A1, which was entered into STN on Mar. 7, 2008, on STN, copyright 2009.*
European Search Report for Application No. 07740014.1-2101/2003127, dated Apr. 23, 2010.

* cited by examiner

Primary Examiner — Janis L Dote
(74) Attorney, Agent, or Firm — Hoffmann & Baron, LLP

(57) ABSTRACT

The present invention discloses a mixed cyclic phenol sulfide which is a mixture of the cyclic phenol sulfide wherein m is 8 and the cyclic phenol sulfide wherein m is an integer other than 8, the cyclic phenol sulfide being represented by the following formula (1):

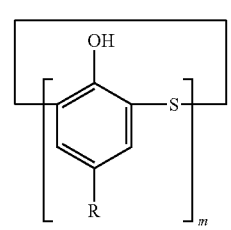

(1)

wherein R is a straight or branched alkyl group having 1 to 6 carbon atoms, and m is an integer from 4 to 9; or a cyclic phenol sulfide of formula (1) wherein m is 8. The present invention also discloses a charge control agent which comprises the above sulfide(s) as the active ingredient; and a toner which comprises the charge control agent, a coloring agent and a binder resin. This charge control agent is particularly useful for color toners, and it speeds up charging risetime, and has a high charge amount and charging characteristics excellent in the environmental stability. Further, the charge control agent is safe since it does not have any problem with the waste regulations.

3 Claims, 10 Drawing Sheets

MIXED CYCLIC PHENOL SULFIDES, AND CHARGE CONTROL AGENTS AND TONERS USING THE SAME

CROSS-REFERENCE TO RELATED APPLICATIONS

This application is a Continuation of International Application No. PCT/JP2007/056576, filed Mar. 28, 2007, which claims the benefit of Japanese Application No. 2006-090976, filed Mar. 29, 2006, the contents of both of which are incorporated by reference herein in their entirety.

FIELD OF THE INVENTION

The present invention relates to charge control agents used in an image forming apparatus which visualizes electrostatic latent images in electrophotography, the electrostatic recording and the like. It also relates to toners having a negative electric containing the charge control agent.

BACKGROUND OF THE INVENTION

In the image forming process according to electrophotography, electrostatic latent images are formed on the inorganic photoreceptor such as selenium, selenium alloy, cadmium sulfide and amorphous silicon or on the organic photoreceptor using a charge generator and a charge transporting agent. Then, the images are developed by a toner, transferred to paper, plastic film or the like and fixed to obtain visible images.

As for photoreceptors, depending on the composition thereof, there are photoreceptors having a positive electric and those having a negative electric. In the case of forming printing parts as electrostatic latent images by exposure, the images are developed by a toner of the opposite sign electrical charge. On the other hand, in the case of reversely developing printing parts by removing the electricity thereof, the images are developed by a toner of the same sign electrical charge. A toner comprises a binder resin, a coloring agent and other additives, and a charge control agent is usually used therein in order to provide desired frictional charge characteristics such as charge speed, charge level, and charge stability, temporal stability, and environmental stability. The charge control agent largely affects the characteristics of a toner.

Further, in the case of color toners, a light-colored and preferably colorless charge control agent is needed, which does not affect the hue. Examples of such light-colored or colorless charge control agents include metal complex salt compounds of hydroxybenzoic acid derivatives (see Patent Literatures 1 to 3), metal salt compounds of aromatic dicarboxylic acid (see Patent Literature 4), metal complex salt compounds of anthranilic acid derivatives (see Patent Literatures 5 and 6), organic boron compounds (see Patent Literatures 7 and 8), biphenol compounds (see Patent Literature 9), calyx(n)arene compounds (see Patent Literatures 10 to 16), and cyclic phenol sulfides (see Patent Literature 16) for a toner having a negative electric; and quaternary ammonium salt compounds (see Patent Literatures 17 to 19) for a toner having a positive electric.

Patent Literature 1: JP-B 55-042752
Patent Literature 2: JP-A 61-069073
Patent Literature 3: JP-A 61-221756
Patent Literature 4: JP-A 57-111541
Patent Literature 5: JP-A 61-141453
Patent Literature 6: JP-A 62-094856
Patent Literature 7: U.S. Pat. No. 4,767,688
Patent Literature 8: JP-A 1-306861
Patent Literature 9: JP-A 61-003149
Patent Literature 10: JP-B 2568675
Patent Literature 11: JP-B 2899038
Patent Literature 12: JP-B 3359657
Patent Literature 13: JP-B 3313871
Patent Literature 14: JP-B 3325730
Patent Literature 15: JP-A 2003-162100
Patent Literature 16: JP-A 2003-295522
Patent Literature 17: JP-A 57-119364
Patent Literature 18: JP-A 58-009154
Patent Literature 19: JP-A 58-098742
Patent Literature 20: JP-A 10-081680

However, many of these charge control agents are complexes or salts which comprise metals such as chromium and zinc, and not always safe since they have a problem with the waste regulations. In addition, such charge control agents are disadvantageous in that they can not be completely colorless; they are late in charging risetime; they have a problem with the environmental stability of the charge amount in hot and humid conditions; the charge amount thereof is low; oppositely-charged toners are numerously generated; or they are poor in dispersibility or stability of the compound. Thus, there has been no compound having satisfactory performance as a charge control agent.

SUMMARY OF THE INVENTION

The object of the present invention is to provide novel mixed cyclic phenol sulfides and specific cyclic phenol sulfides.

The further object of the present invention is to provide charge control agents particularly useful for color toners, which speed up charging risetime, have a high charge amount and charging characteristics excellent in the environmental stability, and are safe since they do not have any problem with the waste regulations.

The additional object of the present invention is to provide toners having a negative electric which comprise said charge control agent having high charging performance.

The present invention has been completed based on the following findings which were obtained by the thorough research to solve the above problems.

Namely, the present invention provides the followings.

1. A mixed cyclic phenol sulfide which is a mixture of cyclic phenol sulfide wherein m is 8 and cyclic phenol sulfide wherein m is an integer other than 8, the cyclic phenol sulfide being represented by the following formula (1):

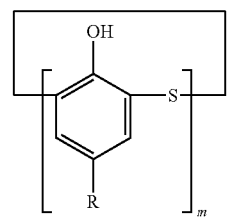

(1)

wherein R is a straight or branched alkyl group having 1 to 6 carbon atoms, and m is an integer from 4 to 9; and
preferably a mixed cyclic phenol sulfide which comprises the cyclic phenol sulfide of the formula (1) wherein m is 4; said cyclic phenol sulfide wherein m is 6; and said cyclic phenol sulfide wherein m is 8.

2. A cyclic phenol sulfide of the formula (1) wherein m is 8.
3. A charge control agent which comprises the above mixed cyclic phenol sulfide or the specific cyclic phenol sulfide as the active ingredient.
4. A toner which comprises the above mixed cyclic phenol sulfide or the specific cyclic phenol sulfide, a coloring agent and a binder resin.

The mixed cyclic phenol sulfide of the present invention is the compound excellent in both the environmental stability and the charge control effect. A quick charging risetime and a high charge amount can be obtained by using the mixed cyclic phenol sulfide of the present invention for a toner, and, as a result, clear images can be obtained.

The charge control agent of the present invention is excellent in the charge control characteristics, the environment resistance and durability. When using it for a toner, it do not induce fogging and it is possible to obtain images with clear image density, high dot reproducibility and high fine line reproducibility.

In a toner containing the mixed cyclic phenol sulfide of the present invention, since the charging characteristics do not vary much in hot and humid conditions or in low and damp conditions, the stable development characteristics can be maintained.

The charge control agent which is the mixed cyclic phenol sulfide of the present invention has a quicker charging risetime, a higher charge amount and charging characteristics more excellent in the environmental stability than those of the conventional charge control agents. Further, it is useful for color toners because it is completely colorless, and it does not contain metals such as chromium and zinc which are concern for the environmental problem. Besides, it is excellent in dispersibility and stability of the compound.

DETAILED DESCRIPTION OF THE INVENTION

Figure 1:
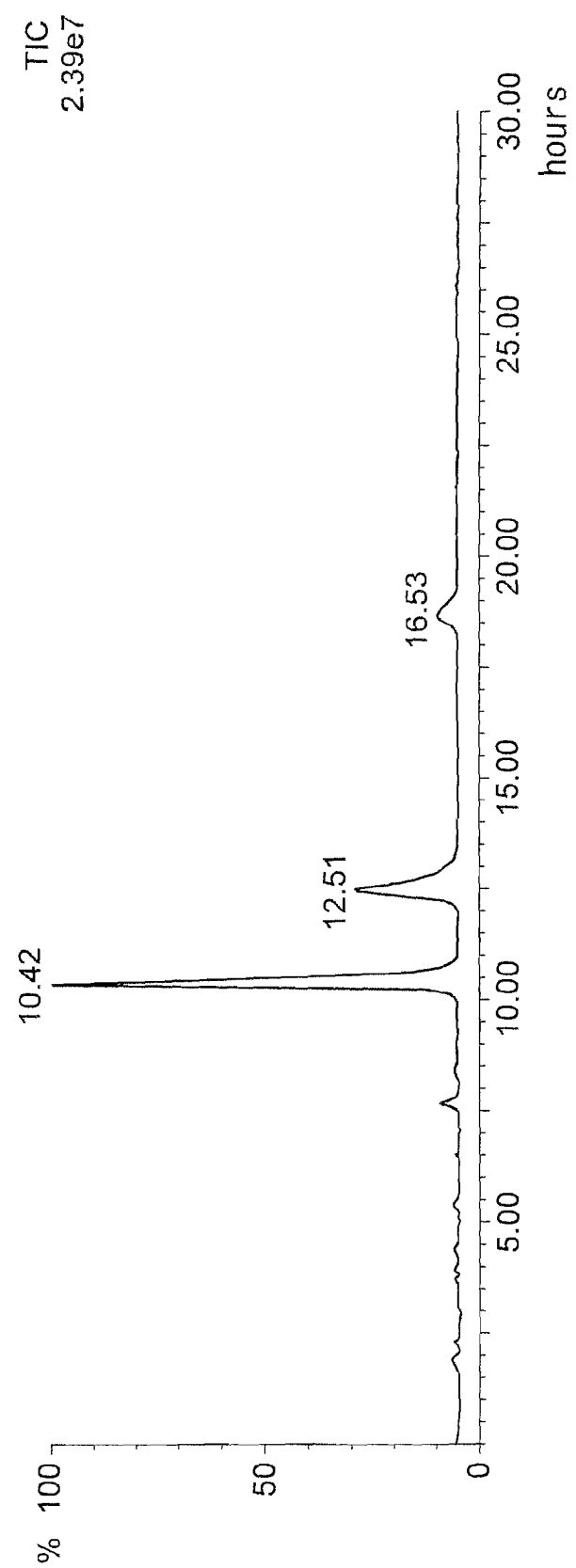
FIG. 1 shows a TIC chart of the mixed cyclic phenol sulfide of Example 1.

In the mixture of the cyclic phenol sulfides of the formula (1), when the total amount of the cyclic phenol sulfides is 100 mol %, it is preferable that the content of the cyclic phenol sulfide wherein m is 8 is 1 mol % or more, more preferably 1.5 mol % or more and particularly preferably 2 mol % or more. Further, it is preferable that the content of the cyclic phenol sulfide wherein m is 8 is 1.5 mol % to 25 mol %, and the content of the cyclic phenol sulfide wherein m is 4 is 75 mol % to 98.5 mol %. It is more preferable that the content of the cyclic phenol sulfide wherein m is 8 is 2 mol % to 15 mol %, and the content of the cyclic phenol sulfide wherein m is 4 is 85 mol % to 98 mol %. In such cases, though the mixture may consist of the cyclic phenol sulfide wherein m is 8 and the cyclic phenol sulfide wherein m is 4, the mixture may further comprise one or more kind(s) of the cyclic phenol sulfide wherein m is 5, the cyclic phenol sulfide wherein m is 6, the cyclic phenol sulfide wherein m is 7 and the cyclic phenol sulfide wherein m is 9.

In the present invention, it is preferable to use the cyclic phenol sulfide wherein m is 6, 7, 8 or 9 by itself, and it is particularly preferable to use the cyclic phenol sulfide wherein m is 8 by itself. More specifically, "by itself" means that, when the total amount of the cyclic phenol sulfides is 100 mol %, the content of the cyclic phenol sulfide wherein m is 8 is 90 mol % or more, preferably 95 mol % or more and particularly preferably substantially 100 mol %.

Examples of straight or branched alkyl groups having 1 to 6 carbon atoms represented by R in the formula (1) include a methyl group, ethyl group, n-propyl group, 2-propyl group, n-butyl group, sec-butyl group, 2-methylpropyl group, tert-butyl group, n-pentyl group, 1-methylbutyl group, 1-ethylpropyl group, 1,1-dimethylpropyl group, 1,2-dimethylpropyl group, n-hexyl group, 1-methylpentyl group, 2-methylpentyl group, 3-methylpentyl group, 4-methylpentyl group, 1-ethylbutyl group, 2-ethylbutyl group, 1,1-dimethylbutyl group, 1,2-dimethylbutyl group, 1,3-dimethylbutyl group, 1,4-dimethylbutyl group, 2,2-dimethylbutyl group, 2,3-dimethylbutyl group, 3,3-dimethylbutyl group, 1-ethyl-2-methyl-propyl group, and 1,1,2-trimethylpropyl group. Among them, alkyl groups having 1 to 4 carbon atoms are preferable, and a butyl group is particularly preferable.

The mixed cyclic phenol sulfide of the present invention can be produced by the publicly known method (refer to Patent Literature 20, for example).

As for the charge control agent of the present invention, it is preferable to adjust the volume average particle diameter to 0.1 to 20 μm for use, and further preferably 0.1 to 10 μm. When the volume average particle diameter is smaller than 0.1 μm, the charge control agent appearing on the toner surface becomes little and the desired charge control effect can not be obtained. When the volume average particle diameter is bigger than 20 μm, the charge control agent dropping from the toner increases and the adverse effects such as contamination in the machine occur.

Examples of the method of making the mixed cyclic phenol sulfide which is a charge control agent used in the present invention contained in a toner include the method comprising the steps of adding it to a binder resin together with a coloring agent and the like, kneading, and crushing them (crushed toner); and the method comprising the steps of adding the mixed cyclic phenol sulfide to polymerizable monomers and polymerizing them to obtain the toner (polymerized toner). Thus, there are the method of adding the mixed cyclic phenol sulfide to the inside of the toner particles in advance (the internal addition) and the method of adding it to the surface of the toner particles which have been produced in advance (the external addition). In the case of internally adding the mixed cyclic phenol sulfide of the present invention to the toner particles, the preferable additive amount thereof is 0.1 to 10 parts by weight to 100 parts by weight of a binder resin, and more preferably 0.2 to 5 parts by weight. In the case of externally adding the mixed cyclic phenol sulfide of the present invention to the toner particles, the preferable additive amount thereof is 0.01 to 5 parts by weight and more preferably 0.01 to 2 parts by weight. Further, it is mechanochemically preferable to fix the mixed cyclic phenol sulfide to the surface of the toner particles.

The charge control agent which comprises the mixed cyclic phenol sulfide of the present invention as the active ingredient can be combined with the other known charge control agent(s) having a negative electric. Examples of the preferable combined charge control agents include azo iron complexes or complex salts, azo chromium complexes or complex salts, azo manganese complexes or complex salts, azo cobalt complexes or complex salts, azo zirconium complexes or complex salts, chromium complexes or complex salts of carboxylic acid derivatives, zinc complexes or complex salts of carboxylic acid derivatives, aluminum complexes or complex salts of carboxylic acid derivatives, and zirconium complexes or complex salts of carboxylic acid derivatives. As for the carboxylic acid derivatives, aromatic hydroxy carboxylic acids are preferable, and more preferably 3,5-di-tert-butyl salicylic acid. In addition, the examples include boron complexes or complex salts, and negative resin charge control agents.

In the case of combining the charge control agent of the present invention with the other charge control agent(s), the preferable additive amount of the charge control agent(s) other than the charge control agent which is the mixed cyclic phenol sulfide of the present invention is 0.1 to 10 parts by weight to 100 parts by weight of a binder resin.

As for the kind of the binder resins used in the present invention, any publicly known one can be used as the binder resin. Examples thereof include vinyl polymers such as styrene monomers, acrylic acid monomers and methacrylic acid monomers or the copolymers comprising two or more kinds of these monomers, polyester polymers, polyol resins, phenol resins, silicone resins, polyurethane resins, polyamide resins, furan resins, epoxy resins, xylene resins, terpene resins, coumarone-indene resins, polycarbonate resins and petroleum resins.

Examples of the styrene monomers, acrylic acid monomers and methacrylic acid monomers which form the vinyl polymers or the copolymers include the followings but not limited to them.

Examples of the styrene monomers are styrenes or derivatives thereof such as styrene, o-methylstyrene, m-methylstyrene, p-methylstyrene, p-phenylstyrene, p-ethylstyrene, 2,4-dimethylstyrene, p-n-amylstyrene, p-tert-butylstyrene, p-n-hexylstyrene, p-n-octylstyrene, p-n-nonylstyrene, p-n-decylstyrene, p-n-dodecylstyrene, p-methoxystyrene, p-chlorostyrene, 3,4-dichlorostyrene, m-nitrostyrene, o-nitrostyrene and p-nitrostyrene.

Examples of the acrylic acid monomers are acrylic acids or esters thereof such as acrylic acids, methyl acrylate, ethyl acrylate, propyl acrylate, n-butyl acrylate, isobutyl acrylate, n-octyl acrylate, n-dodecyl acrylate, 2-ethylhexyl acrylate, stearyl acrylate, 2-chloroethyl acrylate and phenyl acrylate.

Examples of the methacrylic acid monomers are methacrylic acids or esters thereof such as methacrylic acids, methyl methacrylate, ethyl methacrylate, propyl methacrylate, n-butyl methacrylate, isobutyl methacrylate, n-octyl methacrylate, n-dodecyl methacrylate, 2-ethylhexyl methacrylate, stearyl methacrylate, phenyl methacrylate, dimethylaminoethyl methacrylate and diethylaminoethyl methacrylate.

Examples of other monomers which form the vinyl polymers or the copolymers include following (1) to (18): (1) monoolefins such as ethylene, propylene, butylene and isobutylene; (2) polyenes such as butadiene and isoprene; (3) vinyl halides such as vinyl chloride, vinylidene chloride, vinyl bromide and vinyl fluoride; (4) vinyl esters such as vinyl acetate, vinyl propionate and vinyl benzoate; (5) vinyl ethers such as vinyl methyl ether, vinyl ethyl ether and vinyl isobutyl ether; (6) vinyl ketones such as methyl vinyl ketone, hexyl vinyl ketone and methyl isopropenyl ketone; (7) N-vinyl compounds such as N-vinylpyrrole, N-vinylcarbazole, N-vinylindole and N-vinylpyrrolidone; (8) vinylnaphthalenes; (9) acrylic acid or methacrylic acid derivatives such as acrylonitrile, methacrylonitrile and acrylamide; (10) unsaturated dibasic acids such as a maleic acid, citraconic acid, itaconic acid, alkenyl succinic acid, fumaric acid and mesaconic acid; (11) unsaturated dibasic acid anhydrides such as maleic anhydride, citraconic anhydride, itaconic anhydride and alkenyl succinic anhydride; (12) monoesters of unsaturated dibasic acids such as maleic acid monomethylester, maleic acid monoethylester, maleic acid monobutylester, citraconic acid monomethylester, citraconic acid monoethylester, citraconic acid monobutylester, itaconic acid monomethylester, alkenyl succinic acid monomethylester, furamic acid monomethylester and mesaconic acid monomethylester; (13) unsaturated dibasic acid esters such as dimethyl maleate and dimethyl fumarate; (14) α,β-unsaturated acids such as a crotonic acid and cinnamic acid; (15) α,β-unsaturated acid anhydrides such as crotonic anhydride and cinnamic anhydride; (16) monomers having a carboxyl group(s) such as anhydrides of the α,β-unsaturated acid and lower fatty acids, an alkenyl malonic acid, alkenyl glutaric acid, alkenyl adipic acid, and acid anhydrides and monoesters thereof; (17) hydroxyalkyl esters of acrylic acids or methacrylic acids such as 2-hydroxyethyl acrylate, 2-hydroxyethyl methacrylate and 2-hydroxypropyl methacrylate; and (18) monomers having a hydroxyl group such as 4-(1-hydroxy-1-methylbutyl)styrene and 4-(1-hydroxy-1-methylhexyl)styrene.

In the toner of the present invention, vinyl polymers or copolymers of the binder resin may have the cross-linked structure wherein they are cross-linked by a cross-linker having 2 or more vinyl groups. Examples of the cross-linkers used in such a case include aromatic divinyl compounds such as divinylbenzene and divinylnaphthalene. Examples of diacrylate compounds connected by an alkyl chain include ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, or those wherein the acrylate of the above compounds is replaced by methacrylate.

Examples of the diacrylate compounds connected by an alkyl chain including ether bond include diethyleneglycol diacrylate, triethylene glycol diacrylate, tetraethylene glycol diacrylate, polyethylene glycol #400 diacrylate, polyethylene glycol #600 diacrylate, dipropylene glycol diacrylate, or those wherein the acrylate of the above compounds is replaced by methacrylate.

In addition to the above examples, examples also include diacrylate compounds and dimethacrylate compounds connected by a chain including an aromatic group and ether bond. Examples of polyester diacrylates include trade name: MANDA (by Nippon Kayaku Co., Ltd.).

Examples of polyfunctional cross-linkers include pentaerythritol triacrylate, trimethylolethane triacrylate, trimethylolpropane triacrylate, tetramethylolmethane tetraacrylate, oligoester acrylate, those wherein the acrylate of the above compounds is replaced by methacrylate, triallyl cyanurate and triallyl trimellitate.

These cross-linkers can be preferably used in an amount of 0.01 to 10 parts by weight to 100 parts by weight of other monomer components, and particularly preferably used in an amount of 0.03 to 5 parts by weight. Among these cross-linked monomers, examples of the preferably used monomers in a resin for toners in terms of fixity and anti-offset property include aromatic divinyl compounds (particularly preferably divinyl benzene) and diacrylate compounds connected by a binding chain which comprises an aromatic group and one ether bond. Among them, it is preferable to select combination of monomers so as to become a styrene copolymer or a styrene-acrylic acid copolymer.

Examples of polymerization initiators used for producing the vinyl polymer or the copolymer of the present invention include 2,2'-azobisisobutyronitrile, 2,2'-azobis(4-methoxy-2,4-dimethylvaleronitrile), 2,2'-azobis(2,4-dimethylvaleronitrile), 2,2'-azobis(2-methylbutyronitrile), dimethyl-2,2'-azobisisobutyrate, 1,1'-azobis(1-cyclohexanecarbonitrile), 2-(carbamoylazo)-isobutyronitrile, 2,2'-azobis(2,4,4-trimethylpentane), 2-phenylazo-2',4'-dimethyl-4'-methoxyvaleronitrile, 2,2'-azobis (2-methylpropane), ketone peroxides such as methyl ethyl ketone peroxide, acetyl acetone peroxide and cyclohexanone peroxide, 2,2-bis(tert-butyl peroxy)butane, tert-butyl hydroperoxide, cumenehydroperoxide, 1,1,3,3-tetramethyl butyl hydroperoxide, di-tert-butyl peroxide, tert-butyl cumyl peroxide, dicumyl peroxide, α-(tert-butylperoxy)isopropyl benzene, isobutyl peroxide, octanoyl peroxide, decanoyl peroxide, lauroyl peroxide, 3,5,5-trimethyl hexanoyl peroxide, benzoyl peroxide, m-tolyl peroxide, diisopropyl peroxydicarbonate, di-2-ethylhexyl peroxydicarbonate, di-n-propyl peroxydicarbonate, di-2-ethoxyethyl peroxycarbonate, diethoxy isopropyl peroxydicarbonate, bis(3-methyl-3-methoxybutyl)peroxycarbonate, acetyl cyclohexyl sulfonyl peroxide, tert-butyl peroxyacetate, tert-butyl peroxyisobutyrate, tert-butylperoxy-2-ethylhexylate, tert-butyl peroxylaurate, tert-butyloxy benzoate, tert-butylperoxy isopropyl carbonate, di-tert-butyl peroxyisophthalate, tert-butylperoxy allyl carbonate, isoamyl peroxy-2-ethylhexanoate, di-tert-butylperoxy hexahydroterephthalate and tert-butyl peroxyazelate.

When the binder resin is a styrene-acrylic acid resin, in the molecular weight distribution of tetrahydrofuran (hereinafter referred to as THF) soluble parts of the resin component with the gel permeation chromatography (hereinafter referred to as GPC), a resin having at least one peak in the molecular weight area of 3,000 to 50,000 (number-average molecular weight) and having at least one peak in the molecular weight area of 100,000 or more is preferable in terms of fixity, offset property and preservative quality. As for THF soluble parts, the binder resin is preferable wherein the component having the molecular weight area of 100,000 or less is 50 to 90%. Further, a resin having the main peak in the molecular weight area of 5,000 to 30,000 is more preferable, and a resin having the main peak in the molecular weight area of 5,000 to 20,000 is most preferable.

When the binder resin is a vinyl polymer such as a styrene-acrylic acid resin, the acid number thereof is preferably 0.1 mgKOH/g to 100 mgKOH/g, more preferably 0.1 mgKOH/g to 70 mgKOH/g, and further more preferably 0.1 mgKOH/g to 50 mgKOH/g.

Examples of monomers which comprise polyester polymers include, as bivalent alcohols, ethylene glycol, propylene glycol, 1,3-butanediol, 1,4-butanediol, 2,3-butanediol, diethylene glycol, triethylene glycol, 1,5-pentanediol, 1,6-hexanediol, neopentyl glycol, 2-ethyl-1,3-hexanediol, bisphenol A hydride and diols obtained by polymerization of bisphenol A and cyclic ethers such as ethylene oxide and propylene oxide.

It is preferable to combine trivalent or more alcohols in order to cross-link polyester resins. Examples of the trivalent or more alcohols include sorbitol, 1,2,3,6-hexanetetrol, 1,4-sorbitan, pentaerythritol, dipentaerythritol, tripentaerythritol, 1,2,4-butanetriol, 1,2,5-pentatriol, glycerol, 2-methylpropane triol, 2-methyl-1,2,4-butanetriol, trimethylolethane, trimethylolpropane and 1,3,5-trihydroxybenzene.

Examples of the acid components which constitute the polyester polymers include benzene dicarboxylic acids or anhydrides thereof such as a phthalic acid, isophthalic acid and terephthalic acid; alkyl dicarboxylic acids or anhydrides thereof such as a succinic acid, adipic acid, sebacic acid and azelaic acid; unsaturated dibasic acids such as a maleic acid, citraconic acid, itaconic acid, alkenyl succinic acid, fumaric acid and mesaconic acid; and unsaturated dibasic acid anhydrides such as maleic anhydride, citraconic anhydride, itaconic anhydride and alkenyl succinic anhydride. Examples of the polyvalent (trivalent or more) carboxylic acid components include a trimellitic acid, pyromellitic acid, 2,5,7-naphthalene tricarboxylic acid, 1,2,4-naphthalene tricarboxylic acid, 1,2,4-butane tricarboxylic acid, 1,2,5-hexane tricarboxylic acid, 1,3-dicarboxy-2-methyl-2-methylene carboxypropane, tetra(methylene carboxy)methane, 1,2,7,8-octane tetracarboxylic acid, empol trimeric acids, anhydrides thereof, and partially lower alkyl esters.

When the binder resin is a polyester resin, in the molecular weight distribution of THF soluble parts of the resin component, a resin having at least one peak in the molecular weight area of 3,000 to 50,000 is preferable in terms of fixity, anti-offset property and preservative quality. As for THF soluble parts, the binder resin is preferable wherein the component having the molecular weight area of 100,000 or less is 60 to 100%. Further, a resin having at least one peak in the molecular weight area of 5,000 to 20,000 is more preferable.

When the binder resin is a polyester resin, the acid number thereof is preferably 0.1 mgKOH/g to 100 mgKOH/g, more preferably 0.1 mgKOH/g to 70 mgKOH/g, and further more preferably 0.1 mgKOH/g to 50 mgKOH/g.

In the present invention, the molecular weight distribution of the binder resin is determined by GPC using THF as a solvent.

As the binder resin which can be used in the toner of the present invention, it is possible to use, in the vinyl polymer component and/or the polyester resin component, a resin containing a monomer which can react with both resin components. Among the monomers which constitute the polyester resin component, examples of those which can react with the vinyl polymers include unsaturated dicarboxylic acids or anhydrides thereof such as a phthalic acid, maleic acid, citraconic acid and itaconic acid. Examples of the monomers which constitute the vinyl polymer component include those comprising a carboxyl group or a hydroxyl group, acrylic acids or esters of methacrylic acids.

When combining the polyester polymers, vinyl polymers and other binder resins, it is preferable to contain 60 wt % or more of the resin wherein the acid number of the total binder resin is 0.1 to 50 mgKOH/g.

In the present invention, the acid number of the binder resin component of a toner composition is determined by the following method. The basic operation is based on JIS K-0070.
(1) A sample is used after removing additives other than the binder resin (a polymer component), or the acid number and the content of each components other than the binder resin and the cross-linked binder resin are determined in advance. 0.5 to 2.0 g of the crushed sample was precisely weighed. The weight of the polymer component is defined as Wg. For example, when the acid number of the binder resin is determined from a toner, the acid number and the content of each of a coloring agent, a magnetic material or the like are separately determined. Then, the acid number of the binder resin is calculated.
(2) The sample is poured in a 300 mL beaker. Then, 150 mL of a mixed solution of toluene/ethanol (volume ratio=4/1) is added thereto and dissolved.
(3) The mixed solution is tiltrated using 0.1 mol/L of a KOH ethanol solution with a potentiometric tiltrator.
(4) The usage of the KOH solution in (3) is defined as S (mL). At the same time, the blank is determined and the usage of the KOH solution at that time is defined as B (mL). Then, the acid number is calculated using the following formula (1). Meanwhile, f is a factor of the KOH concentration.

$$\text{Acid number}(mgKOH/g)=[(S-B)\times f\times 5.61]/W \quad (1)$$

As for the binder resin of a toner and compositions containing the binder resin, the glass transition temperature (Tg) thereof is preferably 35 to 80° C. and particularly preferably 40 to 75° C., in terms of the preservative quality of a toner. When Tg is lower than 35° C., a toner easily deteriorates in high temperature atmosphere and offset easily occurs upon fixing. When Tg is higher than 80° C., fixity tends to lower.

Examples of the magnetic materials which can be used in the present invention are followings: (1) magnetic iron oxides such as magnetite, maghemite and ferrite, and iron oxides containing other metallic oxides; (2) metals such as iron, cobalt and nickel, or alloyed metals of said metals and the metals such as aluminum, cobalt, copper, lead, magnesium, tin, zinc, antimony, beryllium, bismuth, cadmium, calcium, manganese, selenium, titanium, tungsten and vanadium; and (3) mixtures thereof.

Specific examples of the magnetic materials are $Fe_3O_4$, $\gamma\text{-}Fe_2O_3$, $ZnFe_2O_4$, $Y_3Fe_5O_{12}$, $CdFe_2O_4$, $Gd_3Fe_5O_{12}$, $CuFe_2O_4$, $PbFe_{12}O$, $NiFe_2O_4$, $NdFe_2O$, $BaFe_{12}O_{19}$, $MgFe_2O_4$, $MnFe_2O_4$, $LaFeO_3$, iron powder, cobalt powder and nickel powder. The above mentioned magnetic materials are used by itself or by combination of two kinds or more of them. A particularly preferable magnetic material is fine powders of ferrosoferric oxide or γ-iron sesquioxide.

In addition, magnetic iron oxides such as magnetite, maghemite, ferrite, etc containing dissimilar elements or the mixtures thereof are also usable. Examples of the dissimilar elements include lithium, beryllium, boron, magnesium, aluminum, silicon, phosphorus, germanium, zirconium, tin, sulfur, calcium, scandium, titanium, vanadium, chromium, manganese, cobalt, nickel, copper, zinc and gallium. The preferable dissimilar elements are selected from the group consisting of magnesium, aluminum, silicon, phosphorus and zirconium. The dissimilar elements may be incorporated in the crystal lattice of iron oxides or in the iron oxides themselves as oxides, or they may exist on the surface of iron oxides as oxides or hydroxides. It is preferable that the dissimilar elements are contained as oxides.

The above dissimilar elements can be incorporated in the particles by the steps comprising of mixing salts of each dissimilar elements upon producing a magnetic material, and then adjusting pH thereof. Further, the dissimilar elements can be precipitated on the surface of the particles by the steps comprising of adjusting pH thereof after the production of the magnetic particles, or adding salts of each dissimilar elements and adjusting pH thereof.

The usage of the magnetic materials is 10 to 200 parts by weight and preferably 20 to 150 parts by weight to 100 parts by weight of the binder resin. The number average particle diameter of these magnetic materials is preferably 0.1 to 2 μm and more preferably 0.1 to 0.5 μm. The number average particle diameter can be determined by taking a magnified photograph of the particles with a transmission electron microscope and then measuring it with a digitizer or the like.

As for the magnetic characteristics of the magnetic materials, it is preferable that, when 10K Oersted is applied, the magnetic characteristics are coercivity of 20 to 150 Oersted, saturated magnetization of 50 to 200 emu/g, and remnant magnetization of 2 to 20 emu/g.

The magnetic materials can also be used as coloring agents. Examples of the coloring agents usable in the present invention include, in the case of a black toner, black or blue dye compounds or pigments. Examples of the black or blue pigments include carbon black, aniline black, acetylene black, phthalocyanine blue and indanthrene blue. Examples of the black or blue dye compounds include azo dye compounds, anthraquinone dye compounds, xanthene dye compounds and methine dye compounds.

When using coloring agents for color toners, examples of the coloring agents are the followings. Examples of magenta coloring agents include condensed azo compounds, diketopyrrolopyrrole compounds, anthraquinone compounds, quinacridone compounds, basic dye compounds, lake dye compounds, naphthol dye compounds, benzimidazolone compounds, thioindigo compounds and perylene compounds. More specifically, examples of the pigmentary magenta coloring agents include C.I. pigment red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 184, 202, 206, 207, 209; C.I. pigment violet 19; C.I. vat red 1, 2, 10, 13, 15, 23, 29, 35; methyl violet lake, eosin lake, rhodamine lake B, alizarine lake and brilliant carmine lake 3B.

Though it is acceptable to use the above pigment by itself, it is preferable in terms of the image quality of full-color images to combine the dye compound and the pigment so as to improve the color definition.

Examples of dye magenta coloring agents include oil soluble dye compounds such as C.I. solvent red 1, 3, 8, 23, 24, 25, 27, 30, 49, 81, 82, 83, 84, 100, 109, 121; C.I. disperse red 9; C.I. solvent violet 8, 13, 14, 21, 27; C.I. disperse violet 1; and basic dye compounds such as C.I. basic red 1, 2, 9, 12, 13, 14, 15, 17, 18, 22, 23, 24, 27, 29, 32, 34, 35, 36, 37, 38, 39, 40; and C.I. basic violet 1, 3, 7, 10, 14, 15, 21, 25, 26, 27, 28.

It is possible to use, as cyan coloring agents, copper phthalocyanine compounds and derivatives thereof, anthraquinone, and basic dye lake compounds. More specifically, examples of pigmentary cyan coloring agents include C.I. pigment blue 2, 3, 15, 16, 17; C.I. vat blue 6; C.I. acid blue 45; and copper phthalocyanine pigments wherein 1 to 5 phthalimidemethyl group(s) is substituted to a phthalocyanine skeleton. It is possible to use the agent by blending a green coloring agent such as C.I. pigment green 7, 12, 37 and 38.

Representative examples of phthalocyanine dye compounds include C.I. solvent blue 25, 55, 70; C.I. direct blue 25, 86; alkali blue lake; and victoriablue lake.

Examples of yellow coloring agents include condensed azo compounds, isoindolinone compounds, anthraquinone compounds, azo metal complexes, methine compounds and allylamide compounds. More specifically, examples of yellow pigments include C.I. pigment yellow 1, 2, 3, 4, 5, 6, 7, 10, 11, 12, 13, 14, 15, 16, 17, 23, 65, 73, 83, 97, 180, 185; C.I. vat yellow 1, 3, 20; C.I. solvent yellow 162; quinoline yellow; and tartrazine lake.

The usage of the above coloring agents is preferably 0.1 to 20 parts by weight to 100 parts by weight of the binder resin.

The toner of the present invention may be mixed with a carrier to be used as a two component developer. As for the carriers used in the present invention, it is possible to use both usual carriers such as ferrite and magnetite and resin coated carriers.

The resin coated carrier comprises carrier core particles and a coating material which is a resin coating the surface of the carrier core particles. Preferable examples of the resins used as the coating material include styrene-acrylic acid resin such as styrene-acrylic acid ester copolymers and styrene-methacrylic acid ester copolymers; acrylic acid resins such as acrylic acid ester copolymers and methacrylic acid ester copolymers; fluorine-containing resins such as polytetrafluoroethylene, monochlorotrifluoroethylene polymers and polyvinylidene-fluoride; silicone resins; polyester resins; polyamide resins; polyvinyl butyral; and aminoacrylate resins. In addition to them, examples include resins which can be used as a coating material of the carrier such as iomonomer resins and polyphenylene sulfide resins. These resins are used by itself or by combination of two or more kinds of them.

Besides, a binder carrier core wherein magnetic powders are dispersed in a resin is also usable. As for the method of coating the surface of a carrier core with at least a resin coating agent in a resin coated carrier, it is possible to apply the method comprising the steps of dissolving or dispersing a resin in a solvent, and making the solvent adhere on the carrier core to be coated; or the method of simply mixing a resin in a powdery condition. The ratio of the resin coating material to the resin coated carrier can be arbitrarily determined, and it is preferably 0.01 to 5 wt % to the resin coated carrier and more preferably 0.1 to 1 wt %.

The usage examples of a coating agent comprising a mixture of two or more kinds of compounds for coating a magnetic material include: (1) a coating agent treated with 12 parts by weight of a mixture of dimethyldichlorosilane and dimethyl silicon oil (mass ratio=1:5) to 100 parts by weight of fine powders of a titanium oxide; and (2) a coating agent treated with 20 parts by weight of a mixture of dimethyldichlorosilane and dimethyl silicon oil (mass ratio=1:5) to 100 parts by weight of fine powders of silica.

Among the above resins, a styrene-methyl methacrylate copolymer, a mixture of a fluorine-containing resin and a styrene copolymer, or a silicone resin is preferably used. Particularly, a silicone resin is preferable.

Examples of the mixture of a fluorine-containing resin and a styrene copolymer include a mixture of polyvinylidene-fluoride and a styrene-methyl methacrylate copolymer, a mixture of polytetrafluoroethylene and a styrene-methyl methacrylate copolymer, and a mixture of a vinylidene fluoride-tetrafluoroethylene copolymer (copolymer mass ratio=10:90-90:10), a styrene-acrylic acid-2-ethylhexyl copolymer (copolymer mass ratio=10:90-90:10) and a styrene-acrylic acid-2-ethylhexyl-methyl methacrylate copolymer (copolymer mass ratio=20-60:5-30:10:50).

Examples of the silicone resin include modified silicone resins which are produced by the reaction of a silicone resin with a nitrogen-containing silicone resin(s) and a nitrogen-containing silane coupling agent(s).

As for magnetic materials of a carrier core, it is possible to use oxides such as ferrite, iron excess ferrite, magnetite and γ-iron oxide; metals such as iron, cobalt and nickel; or alloyed metals of said metals. Examples of elements contained in these magnetic materials include iron, cobalt, nickel, aluminum, copper, lead, magnesium, tin, zinc, antimony, beryllium, bismuth, calcium, manganese, selenium, titanium, tungsten and vanadium. The preferable ones are copper-zinc-iron ferrite comprising copper, zinc and iron as main components, and manganese-magnesium-iron ferrite comprising manganese, magnesium and iron as main components.

The resistance value of a carrier is preferably adjusted to $10^6$ to $10^{10}$ Ω/cm by adjusting concavity and convexity of the surface of the carrier and the amount of the resin to be coated. As for the particle diameter of the carrier, though the particle diameter of 4 to 200 μm can be used, 10 to 150 μm is preferable and 20 to 100 μm is more preferable. Particularly, a resin coated carrier preferably has 50% particle diameter of 20 to 70 μm.

In a two component developer, it is preferable to use the toner of the present invention in an amount of 1 to 200 parts by weight to 100 parts by weight of the carrier. It is more preferable to use the toner in an amount of 2 to 50 parts by weight to 100 parts by weight of the carrier.

The toner of the present invention may further contain a wax. Examples of the wax used in the present invention include the followings: aliphatic hydrocarbon waxes such as low-molecular-weight polyethylene, low-molecular-weight polypropylene, polyolefin wax, microcrystalline wax, paraffin wax and SASOL WAX; oxides of aliphatic hydrocarbon waxes such as oxidized polyethylene wax; block copolymers thereof; botanical waxes such as candelilla wax, carnauba wax, Japan wax and jojoba wax; animal waxes such as bees wax, lanolin and whale wax; mineral waxes such as ozokerite, ceresin and petrolatum; waxes comprising fatty acid esters as a main component, such as wax of montanic acid esters and castor wax; and partially or wholly deoxidized fatty acid esters such as deoxidized carnauba wax.

Further examples of the wax include saturated straight fatty acids such as a palmitic acid, stearic acid, montanic acid and straight alkyl carboxylic acids further comprising a straight alkyl group; unsaturated fatty acids such as a brassidic acid, eleostearic acid and parinaric acid; saturated alcohols such as stearyl alcohol, eicosyl alcohol, behenyl alcohol, carnaubil alcohol, ceryl alcohol, mesilyl alcohol and long-chain alkyl alcohol; polyalcohols such as sorbitol; fatty acid amides such as linoleic acid amide, olefinic acid amide and lauric acid amide; saturated fatty acid bisamides such as methylene bis-capric acid amide, ethylene bis-lauric acid amide and hexamethylene bis-stearic acid amide; unsaturated fatty acid amides such as ethylene bisoleic acid amide, hexamethylene bisoleic acid amide, N,N'-dioleyl adipic acid amide and N,N'-dioleyl sebacic acid amide; aromatic bisamides such as m-xylene bis-stearic acid amide and N,N'-distearyl isophthalic acid amide; metallic salts of fatty acids such as calcium stearate, calcium laurate, zinc stearate and magnesium stearate; waxes wherein an aliphatic hydrocarbon wax is grafted by using a vinyl monomer such as styrene and an acrylic acid; partially esterified compounds of polyalcohol and a fatty acid such as behenic acid monoglyceride; and methylester compounds having a hydroxyl group which are obtained by hydrogenating a vegetable oil.

Examples of the preferably used wax include polyolefin obtained by radical-polymerizing olefin under high pressure; polyolefin obtained by purifying a low-molecular-weight by-product obtained in the polymerization of high-molecular-weight polyolefin; polyolefin polymerized under low pressure by using a catalyst such as ZIEGLER CATALYST and metallocene catalyst; polyolefin polymerized by using radiation, electromagnetic wave or light; low-molecular-weight polyolefin obtained by thermally decomposing high-molecular-weight polyolefin; paraffin wax, microcrystalline wax and FISCHER-TROPSCH WAX; synthetic hydrocarbon waxes synthesized by Synthol process, Hydrocol process, Arge process, or the like; synthetic waxes having a compound of one carbon atom as a monomer; hydrocarbon waxes having a functional group such as a hydroxyl group and a carboxyl group; a mixture of a hydrocarbon wax and a hydrocarbon wax having a functional group; and waxes wherein the above waxes are grafted by a vinyl monomer such as styrene, ester maleate, acrylate, methacrylate and maleic anhydride Further, it is preferable to use waxes of which molecular weight distribution is sharpened by treating them with Press sweating process (method), solvents, recrystallization method, vacuum distillation method, supercritical gas extraction method or solution crystallization method; or waxes from which low-molecular-weight solid fatty acids, low-molecular-weight solid alcohols, low-molecular-weight solid compounds or other impurities are removed.

The wax used in the present invention preferably has the melting point of 70 to 140° C. and more preferably 70 to 120° C. in order to balance fixity and anti-offset property. When the melting point is lower than 70° C., the blocking resistance decreases. When the melting point is higher than 140° C., the anti-offset effect is less likely to occur.

Further, combination of two or more different kinds of waxes can develop both the plasticizing action and the mold-releasing action at the same time, each of which is the action of waxes.

Examples of waxes having the plasticizing action are waxes having a low melting point, those having a branched molecular structure, and those having a polar group in the structure. Examples of waxes having the mold-releasing action are waxes having a high melting point, those having a straight molecular structure, and those having nonpolar molecules which do not have any functional group. As usage examples, there are the combination of two or more kinds of waxes between which the difference of the melting points is 10 to 100° C.; and the combination of polyolefin and grafted polyolefin.

When selecting two kinds of waxes, in the case of the waxes having the similar structure, the wax which relatively has lower melting point exerts the plasticizing action, and the wax which relatively has higher meting point exerts the mold-releasing action. At that time, when the difference of each melting points is 10 to 100° C., the functional separation is effectively exerted. When the difference is less than 10° C., the effect of the functional separation is less likely to occur, and when it is more than 100° C., the accentuation of each functions by the interaction is less likely to occur. In such a case, when at least one of the waxes preferably has the melting point of 70 to 120° C. and more preferably 70 to 100° C., the waxes tend to easily exert the effect of the functional separation.

Besides, the wax which relatively has a branched molecular structure, has a polar group such as a functional group or is modified by a component different from the main component exerts the plasticizing action. The wax which relatively has a straight molecular structure, has nonpolar molecules which do not have any functional group or is unmodified and straight exerts the mold-releasing action. Examples of the preferable combination thereof include a combination of polyethylene homopolymer or copolymer having ethylene as the main component and polyolefin homopolymer or copolymer having olefin other than ethylene as the main component; a combination of polyolefin and grafted polyolefin; a combination of a hydrocarbon wax and an alcohol wax, a fatty acid wax or an ester wax; a combination of FISCHER TROPSCH WAX or a polyolefin wax and a paraffin wax or a microcrystalline wax; a combination of FISCHER TROPSCH WAX and a polyolefin wax; a combination of a paraffin wax and a microcrystalline wax; and a combination of a hydrocarbon wax and a carnauba wax, a candelilla wax, a rice bran wax or a montan wax.

In each case, in the endothermic peak observed in the DSC measurement of the toner, it is preferable that the peak-top temperature of the maximum peak is within 70 to 110° C. It is more preferable that the maximum peak is within 70 to 110° C. This makes it easier to balance the preservative quality and the fixity of the toner.

In the toner of the present invention, it is effective to use these waxes in a total content of preferably 0.2 to 20 parts by weight and more preferably 0.5 to 10 parts by weight to 100 parts by weight of the binder resin.

In the present invention, the melting point of a wax is defined as the peak-top temperature of the maximum peak in the endothermic peak of the wax observed in DSC.

In the present invention, it is preferable to conduct the DSC measurement of the wax or the toner with a high-precision intraheater power-compensation type differential scanning calorimeter. The measurement method is based on ASTM D3418-82. The DSC curve used in the present invention is the curve measured when a sample is heated at temperature velocity of 10° C./min. after heating and cooling the sample once and taking a record in advance.

A flow improver may be added to the toner of the present invention. A flow improver improves flowability of the toner (makes it easier to flow) by being added to the surface of the toner. Examples thereof include fluorine resin powders such as carbon black, fine powders of vinylidene fluoride and fine powders of polytetrafluoroethylene; fine powders of silica such as wet processed silica and dry processed silica; fine powders of unoxidized titanium; fine powders of alumina; and treated silica, treated titanium oxide and treated alumina wherein each of the above fine powders is surface-treated with a silane coupling agent, titanium coupling agent or silicone oil. Among them, fine powders of silica, fine powders of unoxidized titanium and fine powders of alumina are preferable, and the treated silica wherein each of said fine powders is surface-treated with a silane coupling agent or silicone oil is further more preferable. The particle diameter of the flow improver is preferably 0.001 to 2 μm as the average primary particle diameter and particularly preferably 0.002 to 0.2 μm.

The preferable fine powders of silica are fine powders produced by oxidizing the gas phase of silicon halides, and referred to as dry processed silica or fumed silica.

Examples of the marketed silica fine powders produced by oxidizing the gas phase of silicon halides include the following trade names: AEROSIL-130, -300, -380, -TT600, -MOX170, -MOX80 and -COK84 (all by Nippon Aerosil Co., Ltd.); Ca-O-SiL-M-5, -MS-7, -MS-75, -HS-5 and -EH-5 (all by CABOT K.K.); WACKER HDK-N20 V15, -N20E, -T30 and -T40 (all by Wacker -Chemie GmbH); D-C FINESILICA (by Dow Corning Toray Co., Ltd.); and FRANSO 1 (by Fransil K.K.).

In addition, treated silica fine powders wherein the silica fine powders produced by oxidizing the gas phase of silicon halides are hydrophobized is more preferable. Among the treated silica fine powders, those each of which is treated so that the hydrophobizing degree thereof measured in methanol titration test preferably indicates 30 to 80% are particularly preferable. Hydrophobizing is given by chemically or physically treating silica fine powders with an organic silicon compound(s) which reacts with silica fine powders or physically adsorbs to them. The preferable method is that comprising the step of treating silica fine powders produced by oxidizing the gas phase of silicon halides with an organic silicon compound(s).

Examples of the organic silicon compound include hydroxypropyl trimethoxysilane, phenyltrimethoxysilane, n-hexadecyltrimethoxysilane, n-octadecyltrimethoxysilane, vinylmethoxysilane, vinyltriethoxysilane, vinyltriacetoxysilane, dimethylvinylchlorosilane, divinylchlorosilane, γ-methacryloxypropyltrimethoxysilane, hexamethyldisilane, trimethylsilane, trimethylchlorosilane, dimethyldichlorosilane, methyltrichlorosilane, allyldimethylchlorosilane, allylphenyldichlorosilane, benzyldimethylchlorosilane, bromomethyldimethylchlorosilane, α-chloroethyltrichlorosilane, β-chloroethyltrichlorosilane, chloromethyldimethylchlorosilane, triorganosilyl mercaptan, trimethylsilyl mercaptan, triorganosilyl acrylate, vinyldimethylacetoxysilane, dimethylethoxysilane, trimethylethoxysilane, trimethylmethoxysilane, methyltriethoxysilane, isobutyltrimethoxysilane, dimethyldimethoxysilane, diphenyldiethoxysilane, hexamethyldisiloxane, 1,3-divinyltetramethyldisiloxane, 1,3-diphenyltetramethyldisiloxane and dimethylpolysiloxane which has 2 to 12 siloxane units per one molecule and contains 0 to 1 hydroxyl group attached to Si in each unit located on ends. Further, examples include silicone oils such as dimethylsilicone oil. Each of the above compounds is used by itself or by a mixture of two or more kinds of them.

The number average particle diameter of the flow improver is preferably 5 to 100 nm and more preferably 5 to 50 nm. The specific surface area thereof by the nitrogen adsorption measured by BET method is preferably 30 $m^2/g$ or more and more preferably 60 to 400 $m^2/g$. The specific surface area of the surface-treated fine powders is preferably 20 $m^2/g$ or more and particularly preferably 40 to 300 $m^2/g$. The preferable applied amount of these fine powders is 0.03 to 8 parts by weight to 100 parts by weight of toner particles.

To the toner of the present invention, it is possible to add other additives such as various metallic soaps, fluorine surfactants and dioctyl phthalate; conductivity giving agents such as tin oxide, zinc oxide, carbon black and antimony oxide; or inorganic fine powders of titanium oxide, aluminum oxide and alumina, if necessary, in order to protect a photoreceptor and a carrier, improve cleaning property, control heat property, electric property, and physical property, control resistance, control softening point and improve the fixation ratio. These inorganic fine powders may be hydrophobized, if necessary. Further, it is possible to use, as an image development improver, a small amount of lubricants such as polytetrafluoroethylene, zinc stearate and polyvinylidene-fluoride; abrasives such as cesium oxide, silicon carbide and strontium titanate; anticaking agents; or white microparticles and black microparticles each of which have the opposite polarity of the toner particles.

It is also preferable to treat the above additives with silicone varnish, various modified silicone varnishes, silicone oil, various modified silicone oils, silane coupling agents, silane coupling agents having a functional group(s), treatment agents such as other organic silicon compounds or various other treatment agents, in order to control the charge amount.

The charge control agent of the present invention can be sufficiently mixed by stirring with the above additive(s) and the toner by a mixer such as HENSCHEL MIXER, a ball mill, NAUTA MIXER, a V-type mixer, a W-type mixer and a supermixer; and said mixture be uniformly externally added to the surface of the toner particles to obtain the subject toner for static electric charge development.

Since the toner of the present invention is thermally stable and not changed by heat in the process of electrophotography, it is possible to maintain stable charging characteristics. In addition, since the toner uniformly disperses in any binder resin, the charging distribution of a fresh toner is fairly uniform. Accordingly, as for the toner of the present invention, changes are hardly seen in both the saturated frictional charge amount and the charging distribution of the untransferable toner and the collected toner (a discarded toner) thereof as compared with those of the fresh toner. However, when reusing the discarded toner collected from the toner for static electric charge image development of the present invention, the gap between the fresh toner and the discarded toner can be further reduced by selecting a polyester resin containing aliphatic diol as the binder resin, or by producing the toner in accordance with the method comprising the steps of selecting a metal-bridged styrene-acrylic acid copolymer as the binder resin and adding large quantities of polyolefin thereto.

As for the method of producing the toner of the present invention, the toner can be produced by the known production method. For example, the preferable production method is the method (crushing method) comprising the steps of sufficiently mixing the above mentioned toner constituent materials such as a binder resin, a charge control agent and a coloring agent by a mixer such as a ball mill; then, sufficiently kneading the mixture by a heat kneading machine such as a heat roll kneader; solidifying by cooling, crushing and classifying the mixture to obtain a toner.

The toner can also be produced by dissolving the above mixture in a solvent, atomizing, drying and classifying it. Further, the toner can also be produced by the polymerization method, which comprises the steps of mixing specific materials to a monomer constituting the binder resin to prepare an emulsion or a suspension, and polymerizing the solution. As for a microcapsule toner comprising a core material and a shell material, such toner can be produced by the method comprising the step of making specific materials contain in a core material or a shell material, or both of them. Further, if necessary, the toner of the present invention can be produced by sufficiently mixing a needed additive(s) and toner particles by a mixer such as HENSCHEL MIXER.

The method of producing the toner of the present invention by the above crushing method is further illustrated as follows. First, a binder resin, a coloring agent, a charge control agent and other necessary additives are uniformly mixed. They can be mixed with a known mixer such as HENSCHEL MIXER, a supermixer and a ball mill. The obtained mixture is heat-molten and kneaded with a hermetically sealed kneader or a single or double screw extruder. After cooling down the kneaded mixture, it is coarsely crushed with a crusher or a hammer mill, and then finely milled with a pulverizer such as a jet mill and a high-speed rotor whirling mill. Then, the obtained powders are classified to a specific particle size with a wind force classifier such as Elbow-jet of an inertial classification system utilizing the Coanda effect, Microplex of a cyclone (centrifugal) classification system or a DS separator. When further adding an external additive(s) to the surface of the toner, the toner and the external additive(s) are stirred and mixed with a high-speed mixer such as HENSCHEL MIXER and a supermixer.

The toner of the present invention can also be produced by the suspension polymerization method or the emulsion polymerization method. The suspension polymerization method comprises the following steps. A polymerizable monomer, a coloring agent, a polymerization initiator, a charge control agent and, if necessary, a cross-linker and other additives are uniformly dissolved or dispersed to prepare a monomer composition. The monomer composition is dispersed in the continuous phase containing a dispersion stabilizer and said composition such as the aqueous phase with a suitable mixer or disperser such as a homomixer, a homogenizer, an atomizer, a microfluidizer, a one-fluid nozzle, a gas-liquid fluid nozzle and an electric emulsifying machine. Preferably, the stirring speed, temperature and time are controlled so that droplets of the polymerizable monomer composition have the desired toner particle size, and granulation is conducted. At the same time, the polymerization reaction is conducted at 40 to 90° C. to be able to obtain toner particles having the desired particle diameter. The obtained toner particles are washed, filtered out and dried. As for the external addition after producing the toner particles, the above mentioned method can be used.

When producing the toner by the emulsion polymerization method, though the toner particles thereof are more uniform than those obtained by the suspension polymerization method, the average particle diameter thereof is 0.1 to 1.0 μm and extremely small. Therefore, in some cases, a toner can be produced by the seed polymerization in which an emulsified particle becomes a core and a polymerizable monomer is added thereto afterward to grow the particle, or by the method comprising the steps of unifying and fusing emulsified particles to a suitable average particle diameter.

According to the production of the toner by these polymerization methods, since there is no crushing process, there is no need to give brittleness to toner particles. Thus, it is possible to use large amounts of substances having a low softening point, of which use was difficult in prior crushing methods, and that makes it possible to widen choices of materials. Further, since a mold-releasing agent or a coloring agent each of which is a hydrophobizing material is not easily exposed on the surface of the toner particles, it is possible to decrease contamination in a toner support member, a photoreceptor, a transferring roller, a fixing machine or the like.

The production of the toner of the present invention by the polymerization method can further improve properties such as image reproducibility, transferability and color reproducibility. Further, a toner having a sharp particle size distribution can be comparatively easily obtained by minimizing the particle diameter of the toner in order to apply to tiny dots.

As for the polymerizable monomer used in producing the toner of the present invention by the polymerization method, a vinyl polymerizable monomer of which radical polymerization is possible is used. As the vinyl polymerizable monomer, a monofunctional polymerizable monomer or a polyfunctional polymerizable monomer can be used.

Examples of the monofunctional polymerizable monomer include styrene polymerizable monomers such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene and p-phenylstyrene; acrylic acid polymerizable monomers such as methyl acrylate, ethyl acrylate, n-propyl acrylate, isopropyl acrylate, n-butyl acrylate, isobutyl acrylate, tert-butyl acrylate, n-amyl acrylate, n-hexyl acrylate, 2-ethylhexyl acrylate, n-octyl acrylate, benzyl acrylate, dimethylphosphate methyl acrylate, dibutylphosphate ethyl acrylate and 2-benzoyloxy ethyl acrylate; methacrylic acid polymerizable monomers such as methyl methacrylate, ethyl methacrylate, n-propyl methacrylate, isopropyl methacrylate, n-butyl methacrylate, isobutyl methacrylate, tert-butyl methacrylate, n-amyl methacrylate, n-hexyl methacrylate, 2-ethylhexyl methacrylate, n-octyl methacrylate, diethylphosphate methacrylate and dibutylphosphate ethyl methacrylate; unsaturated aliphatic monocarboxylic acid esters; vinyl esters such as vinyl acetate, vinyl propionate and vinyl benzoate; vinyl ethers such as vinyl methyl ether and vinyl isobutyl ether; and vinyl ketones such as methyl vinyl ketone, hexyl vinyl ketone and isopropyl vinyl ketone.

Examples of the water-soluble initiator include ammonium persulfate, potassium persulfate, 2,2'-azobis(N,N'-dimethylene isobutyroamidine) hydrochloride, 2,2'-azobis(2-aminodipropane) hydrochloride, azobis(isobutylamidine) hydrochloride, 2,2'-azobisisobutyronitrile sodium sulfonate, ferrous sulfate and hydrogen peroxide.

The additive amount of a polymerization initiator is preferably 0.5 to 20 parts by weight to 100 parts by weight of a polymerizable monomer. The polymerization initiator may be used by itself or by combination thereof. Examples of the dispersant used in the production of a polymerized toner include inorganic oxides such as tricalcium phosphate, magnesium phosphate, aluminum phosphate, zinc phosphate, calcium carbonate, magnesium carbonate, aluminum hydroxide, calcium metasilicate, calcium sulfate, barium sulfate, bentonite, silica and alumina. As for organic compounds, for example, polyvinyl alcohol, gelatin, methylcellulose, methylhydroxypropylcellulose, ethyl cellulose, sodium salt of carboxymethylcellulose, starch, or the like is used. These dispersants are preferably used in an amount of 0.2 to 2.0 parts by weight to 100 parts by weight of a polymerizable monomer.

Though the marketed dispersants may be used as they are, in order to obtain fine disperse particles having a uniform particle size, the above inorganic compounds can also be produced by high-speed stirring in a disperse medium.

As for the toner obtained by the polymerization method, the concavity and convexity of the toner particles tend to be smaller than those of the toner obtained by the crushing method in which special treatment is not conducted. Since such toner particles are amorphous, the contact area between an electrostatic latent image support member and the toner increases, and it makes the toner adhesion stronger. As a result, the contamination in the machine is decreased and it becomes easier to obtain higher image density and higher quality images.

As for the toner produced by the crushing method, the concavity and convexity of the toner surface can be decreased by the methods such as the hot-water bath method which comprises the steps of dispersing toner particles in water and heating the solution; heat treatment method comprising the step of making toner particles pass through thermal current; and the mechanical impact method comprising the step of treating the particles by giving the mechanical energy. Examples of the effective equipments for decreasing the concavity and convexity include a MECHANOFUSION SYSTEM (by Hosokawa Micron Corp.) applying the dry mechanochemical treatment; an I-TYPE JET MILL; a HYBRIDIZER (by Nara Machinery Co., Ltd.) which is a mixing equipment with a rotor and a liner; and HENSCHEL MIXER which is a mixer having high-speed blades.

As one of the values which show the degree of the concavity and convexity of the toner particles, an average circularity degree can be used. The average circularity degree (C) indicates the value which is calculated as follows. First, a circularity degree (Ci) is calculated by the following formula (2). Then, the sum of the circularity degrees of all measured particles is divided by the number of all measured particles (m) as mentioned in the following formula (3).

$$\text{Circularity degree } (Ci) = \frac{\text{Boundary length of the circle having the same projected area as that of a particle}}{\text{Boundary length of the projected image of a particle}} \quad (2)$$

$$\text{Average circularity degree } C = \sum_{i=1}^{m} \frac{Ci}{m} \quad (3)$$

The above circularity degree (Ci) is measured using a flow particle image analyzer such as FPIA-1000 by TOA Medical Electronics Co., Ltd. As for the measurement method, first, about 5 mg of a toner is dispersed in 10 mL of water in which about 0.1 mg of a nonionic surfactant is dissolved to prepare a dispersion solution. Ultrasonic wave (20 kHz, 50 W) is irradiated to the dispersion solution for 5 minutes, and the solution is prepared to become the concentration of 5000 to 20000/µL. Then, the distribution of the circularity degree of a particle having the diameter which is equivalent to the circle of 0.60 µm or more and less than 159.21 µm is measured with the flow particle image analyzer.

The value of the average circularity degree is preferably 0.955 to 0.990. It is further preferable to prepare toner particles so that the value becomes 0.960 to 0.985 since events which cause the increase in the left toner after transferring decrease and another transferring tends not to easily occur.

In the case of the toner of the present invention, in terms of clear images and productivity of the toner, the particle diameter of the toner is preferably 2 to 15 µm in the average particle diameter on volumetric basis in the measurement with a laser particle size distribution analyzer such as a micron sizer by Seishin Enterprise Co., Ltd, for example. 3 to 12 µm thereof is more preferable. When the average particle diameter is beyond 15 µm, the resolution or sharpness of images tends to weaken. When the average particle diameter is less than 2 µm, though the resolution becomes better, it costs more because of the decrease in the yield rate upon production of a toner. Further, a toner spatters in the machine, or health disorders such as skin penetration tend to occur.

As for the particle size distribution of a toner, in the case of the toner of the present invention, it is preferable that the content of particles of 2 µm or smaller accounts for 10 to 90% on number basis of the toner, which is measured by a COULTER counter (TA-II, by Coulter K. K.), for example. Besides, it is preferable that the content of particles of 12.7 µm or larger accounts for 0 to 30% on volumetric basis of the toner.

In the case of the toner for static electric charge development of the present invention, it is preferable that the specific surface area of the toner is 1.2 to 5.0 $m^2/g$ according to the BET specific surface area measurement wherein nitrogen is used as deadsorption gas. It is more preferable that the specific surface area is 1.5 to 3.0 $m^2/g$. The measurement of the specific surface area comprises the steps, for example, of desorbing adsorption gas on the surface of the toner at 50° C. for 30 minutes with a BET specific surface area measurement device (such as FlowSorbII2300 by Shimadzu Corporation); adsorbing nitrogen gas again by rapidly cooling down the toner with liquid nitrogen; and then heating it again up to 50° C. The specific surface area is defined as the value calculated from the amount of desorbed gas at that time.

In the case of the toner of the present invention, the apparent ratio (the powder density) thereof is measured with a powder tester (by Hosokawa Micron Corp., for instance), for example. The ratio of a non-magnetic toner is preferably 0.2 to 0.6 $g/cm^3$. The ratio of a magnetic toner is preferably 0.2 to 2.0 $g/cm^3$, though it depends on a kind of magnetic powders or the content thereof.

In the case of the toner of the present invention, the absolute specific gravity of a non-magnetic toner is preferably 0.9 to 1.2 $g/cm^3$. The absolute specific gravity of a magnetic toner is preferably 0.9 to 4.0 $g/cm^3$, though it depends on a kind of magnetic powders or the content thereof. The absolute specific gravity of the toner is calculated as follows. 1.000 g of the toner is precisely weighed, poured in a 10 mmφ tableting machine and compressed at a pressure of 200 $kgf/cm^2$ under vacuum to make tablets. The height of this columnar tablet is measured with a micrometer, and the absolute specific gravity is calculated therefrom.

The flowability of a toner is defined, for example, by a flowing repose angle and a still repose angle measured by a device for measuring the angle of repose (for example, by Tsutsui Scientific Instruments Co., Ltd.). In the case of the toner for static electric charge development wherein the charge control agent of the present invention is used, a flowing repose angle is preferably 5 to 45° and a still repose angle is preferably 10 to 50°.

As for the toner of the present invention, the average value of shape factor (SF-1) of the crushed toner is preferably 100 to 400; and the average value of shape factor 2 (SF-2) thereof is preferably 100 to 350.

In the present invention, SF-1 and SF-2 each of which indicates shape factor of the toner were calculated as follows, for example. Toner particles magnified 1000 diameters were taken as a sample so that around 30 particles appear in one visual field by using a light microscope with a CCD camera (such as BH-2 by Olympus Corporation). The obtained image was transferred to an image analyzer (such as LUZEX FS by Nireco Corporation). The same procedure was repeated until the number of toner particles reaches about 1000 and the shape factor was calculated. Shape factor (SF-1) and shape factor 2 (SF-2) are calculated by the following formulae.

$$SF\text{-}1 = ((ML^2 \times \pi)/4A) \times 100$$

wherein, ML is the maximum length of particles; A is a projected area of one particle, $$SF\text{-}2 = (PM^2/4A\pi) \times 100$$

wherein, PM is the peripheral length of particles; A is a projected area of one particle.

SF-1 indicates deformation of a particle. SF-1 becomes closer to 100 when a particle becomes closer to a sphere, and the slenderer a particle is, the larger SF-1 is. SF-2 indicates concavity and convexity of a particle. SF-2 becomes closer to 100 when a particle becomes closer to a sphere, and the more complicated the shape of a particle is, the larger SF-2 is.

The volume resistivity of the toner of the present invention is preferably $1 \times 10^{12}$ to $1 \times 10^{16}$ Ω·cm in the case of a non-magnetic toner. The volume resistivity of a magnetic toner is preferably $1 \times 10^8$ to $1 \times 10^{16}$ Ω·cm, though it depends on a kind of magnetic powders or the content thereof. Here, the volume resistivity of the toner is defined as follows. Toner particles are compressed to prepare a disk-shaped test piece of 50 mm in diameter and 2 mm thick. This piece is set to electrodes for solid materials (such as SE-70 by Ando Electric Co., Ltd.), and direct voltage 100V is continuously applied to the piece. Then, the value thereof one hour later is measured with a high insulation resistance meter (for example, 4339A by Hewlett-Packard Company) and defined as the volume resistivity.

The dielectric tangent of the toner of the present invention is preferably $1.0 \times 10^{-3}$ to $15.0 \times 10^{-3}$ in the case of a non-magnetic toner. The dielectric tangent of a magnetic toner is preferably $2 \times 10^{-3}$ to $30 \times 10^{-3}$, though it depends on a kind of magnetic powders or the content thereof. Here, the dielectric tangent of the toner is defined as follows. Toner particles are compressed to prepare a disk-shaped test piece of 50 mm in diameter and 2 mm thick. This piece is set to electrodes for solid materials and measured in measurement frequency of 1 KHz and peak-to-peak voltage 0.1 KV with a LCR meter (for example, 4284A by Hewlett-Packard Company). Thus obtained value is defined as the dielectric tangent value (Tan δ).

The Izod impact level of the toner of the present invention is preferably 0.1 to 30 kg·cm/cm. Here, the Izod impact level of the toner is measured by the method comprising the steps of fusing toner particles by heat to prepare a plate-like test piece; and measuring the pieces in accordance with JIS K-7110 (Izod impact test of rigid plastic).

The melt index (MI) of the toner of the present invention is preferably 10 to 150 g/10 min. Here, MI of the toner is measured in accordance with JIS K-7210 (A method), and at that time, the measurement temperature is 125° C. and weight is 10 kg.

The melting start temperature of the toner of the present invention is preferably 80 to 180° C., and 4 mm descent temperature is preferably 90 to 220° C. Here, the melting start temperature of the toner is measured by the following method. Toner particles are compressed to prepare a column-shaped test piece of 10 mm in diameter and 20 mm thick. This piece is set to a thermofusion property measurement device such as a flowtester (for example, CFT-500C by Shimadzu Corporation) and measured in load of 20 kgf/cm². Under such condition, the temperature at which the fusion starts and a piston starts to descend is defined as the melting start temperature. Further, in the same measurement, the temperature at which the piston descends 4 mm is defined as 4 mm descent temperature.

The glass transition temperature (Tg) of the toner of the present invention is preferably 35 to 80° C., and more preferably 40 to 75° C. Here, the glass transition temperature of the toner is measured with a differential scanning calorimetry (hereinafter referred to as DSC) by the method comprising the steps of heating the toner at a constant temperature, rapidly cooling it down, and heating it again. Tg is defined as the value determined from the peak of phase-change which occurs at that time. When Tg of the toner is lower than 35° C., anti-offset property or preservative quality thereof tends to deteriorate. When Tg is higher than 80° C., the fixity level of images tends to deteriorate.

In the endothermic peak observed in the DSC measurement of the toner of the present invention, it is preferable that the peak-top temperature of the maximum peak is within 70 to 120° C.

The melt viscosity of the toner of the present invention is preferably 1000 to 50000 poise and more preferably 1500 to 38000 poise. Here, the melt viscosity of the toner is measured as follows. Toner particles are compressed to prepare a column-shaped test piece of 10 mm in diameter and 20 mm thick. These pieces are set to a thermofusion property measurement device such as a flowtester (for example, CFT-500C by Shimadzu Corporation) and measured in load of 20 kgf/cm². Thus measured value is defined as the melt viscosity.

The dissolving residue of a solvent of the toner of the present invention is preferably 0 to 30 wt % as THF insoluble matter, 0 to 40 wt % as ethyl acetate insoluble matter, and 0 to 30 wt % as chloroform insoluble matter. Here, the dissolving residue of a solvent is calculated as follows. 1 g of toner is uniformly dissolved or dispersed in of each 100 mL solvent of THF, ethyl acetate and chloroform. The solution or dispersion solution is press filtered and a filtrate is dried and quantitated. The ratio of an insoluble substance to an organic solvent in the toner is calculated from the quantitated value and defined as the dissolving residue of a solvent.

The toner of the present invention can be used in the one-component development process, which is one of the image forming processes. The one-component development process is the process comprising the steps of providing a latent image support member with the thinned toner, and developing the latent images. The toner is usually thinned with a device wherein a toner carrying material, a toner layer thickness controlling material and a toner supply auxiliary material are equipped; and the toner supply auxiliary material and the toner carrying material, and the toner layer thickness controlling material and the toner carrying material abut each other.

The case in which the toner of the present invention is used in the two-component development process is further illustrated as follows. The two-component development process is the process wherein a toner and a carrier (those having roles as a charge provider and a toner carrying material) are used. The above magnetic materials or glass beads are used as a carrier. Developers (toner and a carrier) generate a specific charge amount by being stirred by a stirring material, and they are carried to a developing part by a magnet roller or the like. On the magnet roller, the developers are kept on the surface of the roller by magnetic force, and they form a magnetic brush whose layer is controlled to a suitable height by a developer control plate or the like. The developers move on the development roller as the roller rotates, and contact with an electrostatic latent image support member or face against it in a specific distance and in the noncontact condition to develop and visualize latent images. When developing images in the noncontact condition, a toner can usually obtain the driving force of flying the space of a specific distance by generating a direct electric field between developers and a latent image support member. However, in order to develop clearer images, it is possible to apply the method of superimposing alternating current.

Further, the charge control agent of the present invention is suitable for a charge control agent (a charge enhancer) in coating compounds for coating electrostatic powders. Namely, coating compounds for coating electrostatic powders using said charge enhancer are excellent in environment resistance and preservation stability, and particularly thermal stability and durability. Besides, the coating efficiency thereof reaches 100% and, therefore, it is possible to form thick film without coating defect.

Next, Examples will further illustrate the present invention. They only explain the present invention and do not particularly limit the invention.

EXAMPLE 1

130.3 g of 4-tert-butylphenol, 110.9 g of sulfur and 28.3 g of potassium hydroxide were poured in a 1 L four-neck flask with a mixer, a cooling tube, a thermometer and a gas-introducing tube. 40 mL of tetraethylene glycol dimethyl ether was added thereto and stirred in the current of nitrogen gas while keeping it at 130° C. The reaction was conducted for 2 hours with removing water and hydrogen sulfide each of which was generated in the reaction. After heating it up to 180° C., the reaction was further conducted for 4 hours with removing water and hydrogen sulfide each of which was generated in the reaction. The reaction mixture was cooled down to room temperature, and 1500 mL of diethyl ether was added thereto and hydrolyzed with 1 mol/L of a diluted sulfuric acid. The organic layer was isolated, concentrated and dried to obtain 124.8 g of the reaction mixture.

12.8 g of sulfur, 11.2 g of calcium oxide, 22 mL of ethylene glycol and 86 mL of tetraethylene glycol dimethyl ether were added to 103.2 g of the reaction mixture and stirred in the current of nitrogen gas while keeping the suspension at 130° C. The reaction was conducted for 2 hours with removing water and hydrogen sulfide each of which was generated in the reaction. The reaction was further conducted for 2 hours after heating it up to 170° C., and then for 3.5 hours after heating it up to 230° C., with removing water and hydrogen sulfide each of which was generated in the reaction. The reaction mixture was cooled down to room temperature, and 500 mL of toluene and diethyl ether were added thereto and hydrolyzed with 1 mol/L of a diluted sulfuric acid. The organic layer was isolated, concentrated and dried, and then the obtained mixture was purified with a column chromatography (carrier: silica gel 5 Kg; eluent: hexane/chloroform) to obtain 46.8 g of a mixed cyclic phenol sulfide of the present invention.

The structure of the mixed cyclic phenol sulfide of the present invention was analyzed by LC/MS measurement. The measurement condition of LC/MS is as follows: (1) HPLC measurement condition: device: 2695 by Nihon Waters K. K.; column: CAPCELL PAK C18ACR by Shiseido Co., Ltd. (5μ, inside diameter 4.6, column length 250mm); column temperature: 40° C.; mobile phase: tetrahydrofuran (hereinafter referred to as THF)/acetonitrile/water/trifluoroacetic acid =450/400/150/2 (v/v/v/v); current speed: 1.0mL/min.; filling amount: 1 μL; and concentration of a sample: 2000ppm; (2) MS measurement condition: device: QUATROMICRO API MASS SPECTROMETER by Micromass K.K.; ionization method: ESI (positive mode); capillary voltage: 2.80 KV; flow rate of desolvating gas: 500 L/hour; temperature of desolvating gas: 350° C.; temperature of ion source: 120° C.; and cone voltage: 40 to 60V.

Figure 2:
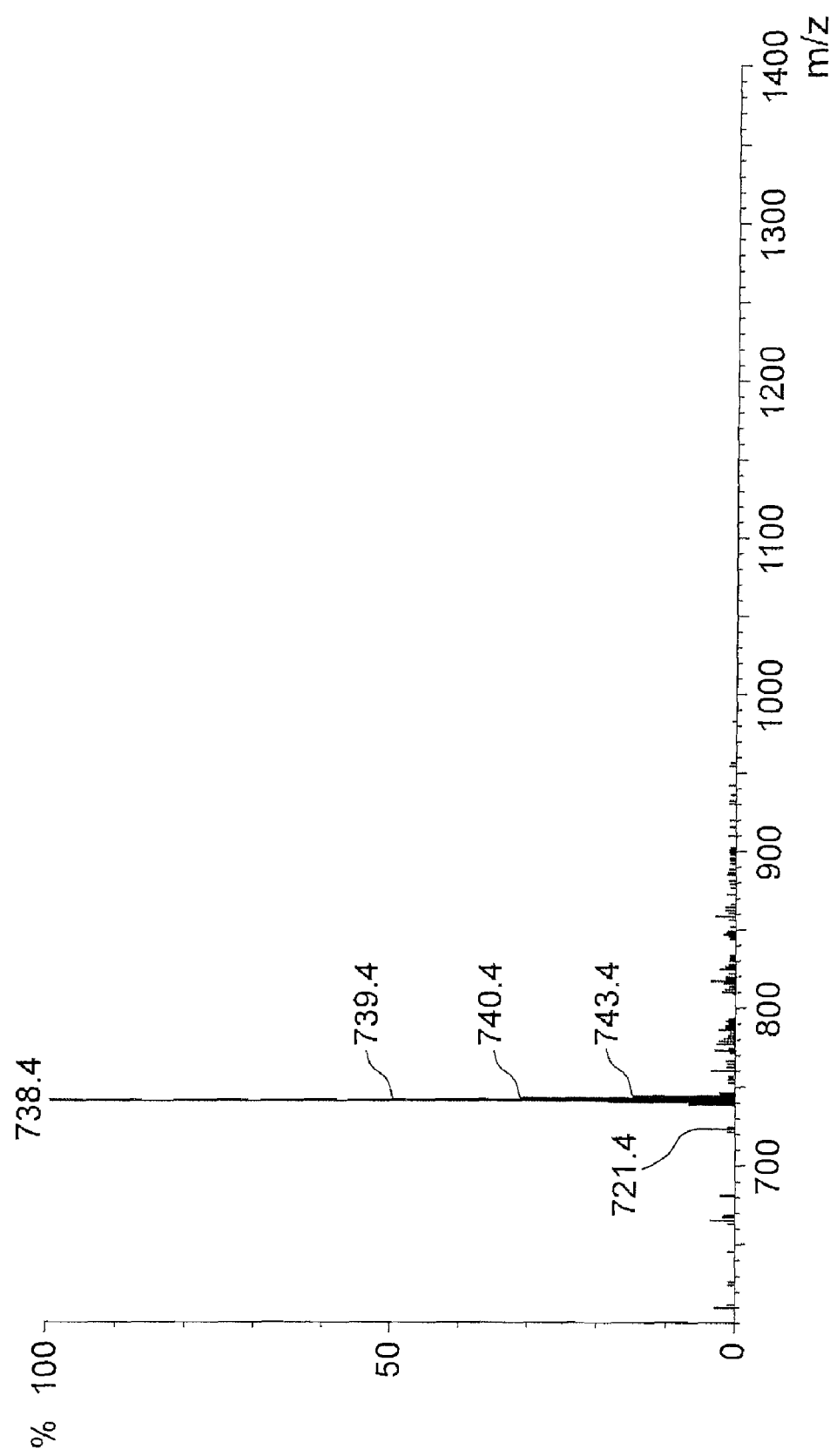
FIG. 2 shows a MS chart of TC4A.
Figure 3:
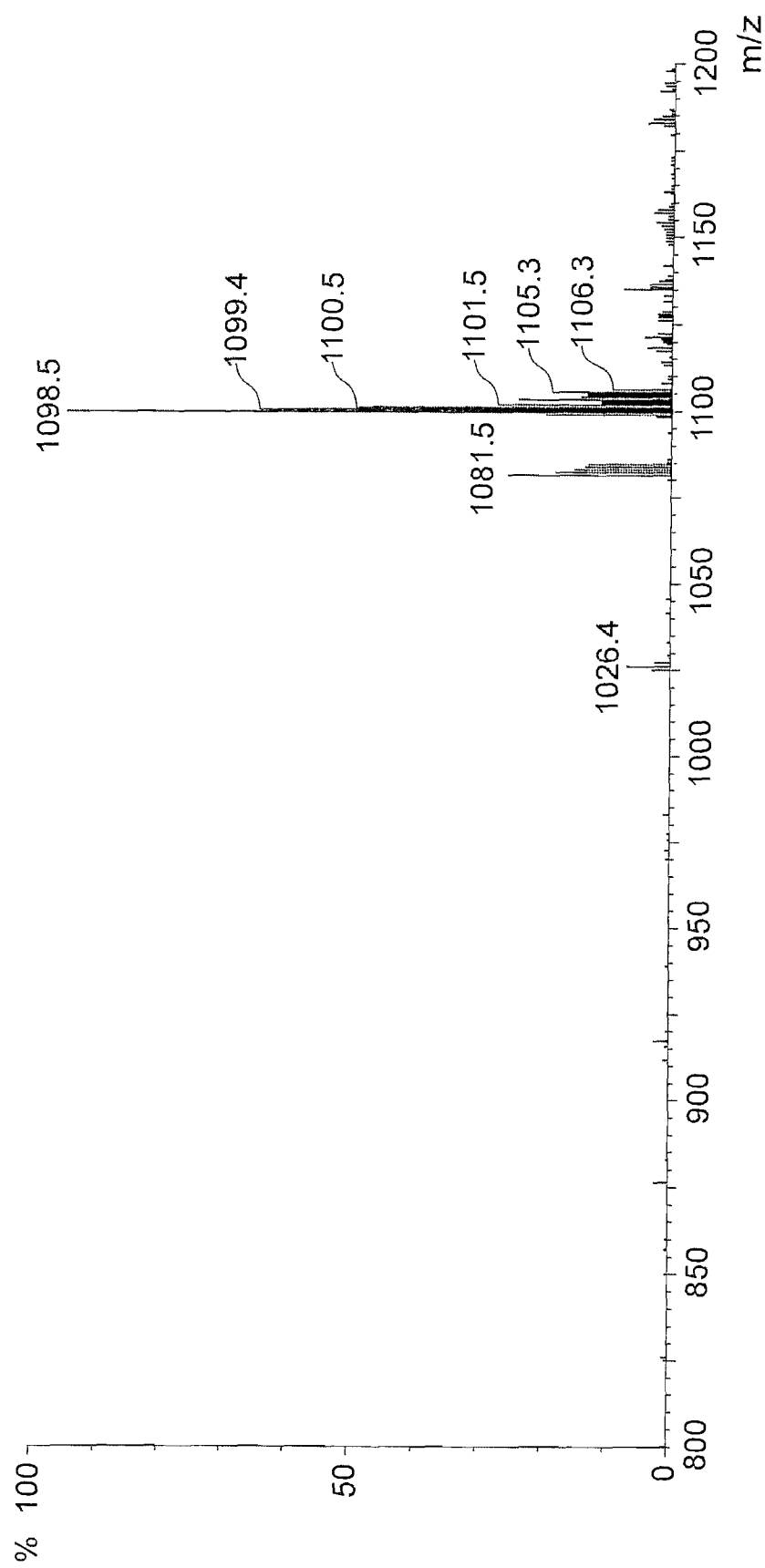
FIG. 3 shows a MS chart of TC6A.
Figure 4:
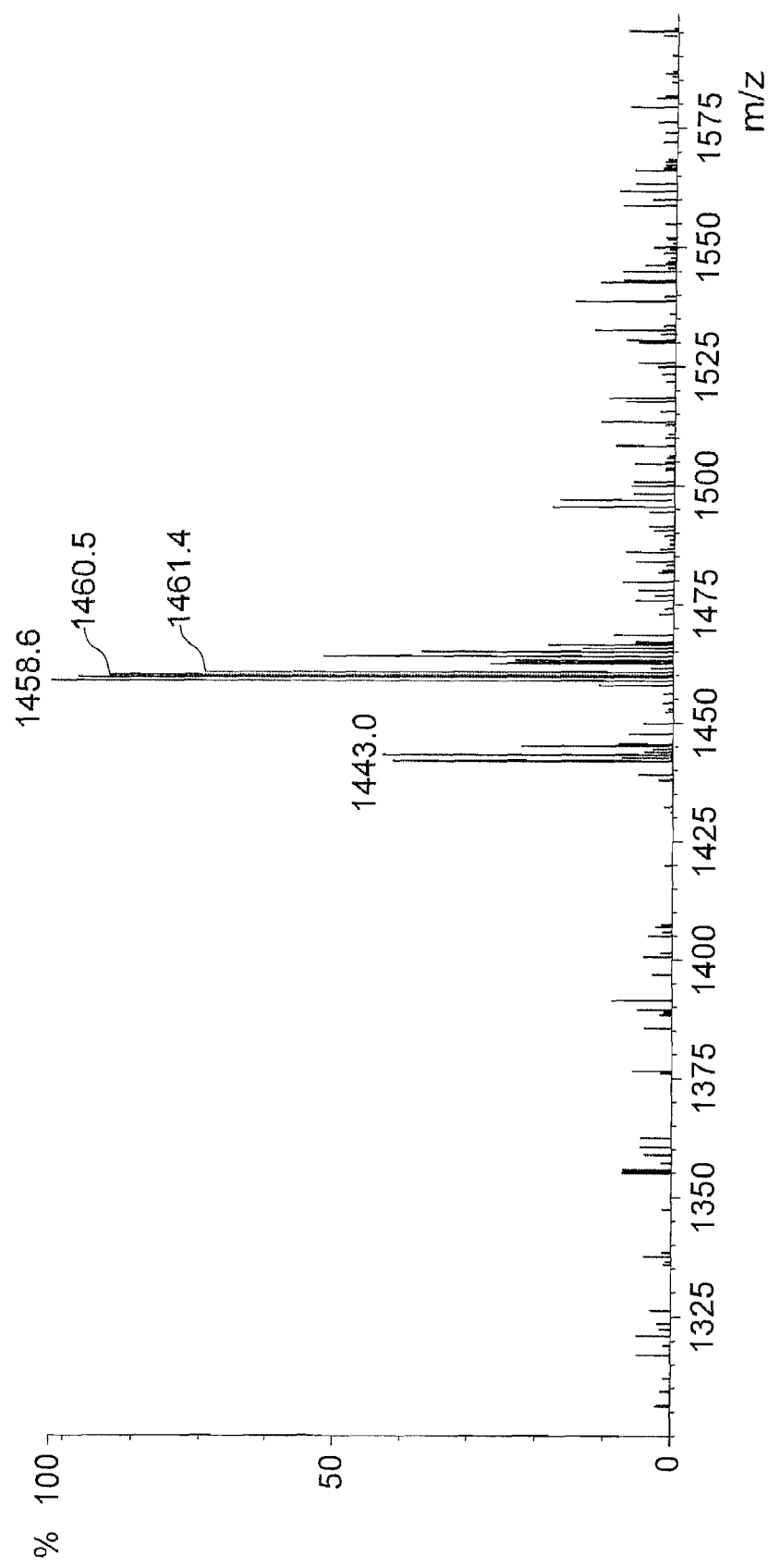
FIG. 4 shows a MS chart of TC8A.
Figure 5:
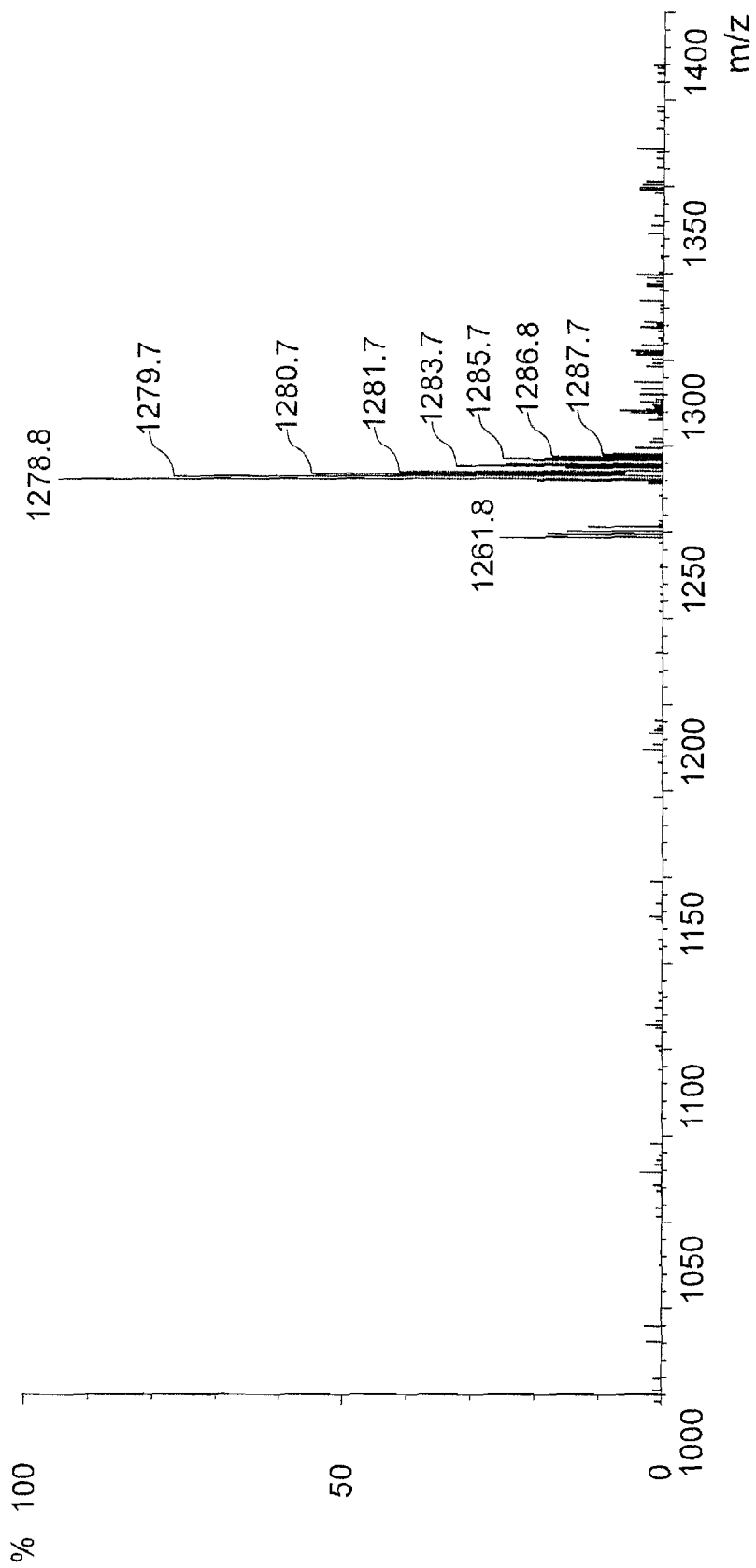
FIG. 5 shows a MS chart of TC7A.
Figure 6:
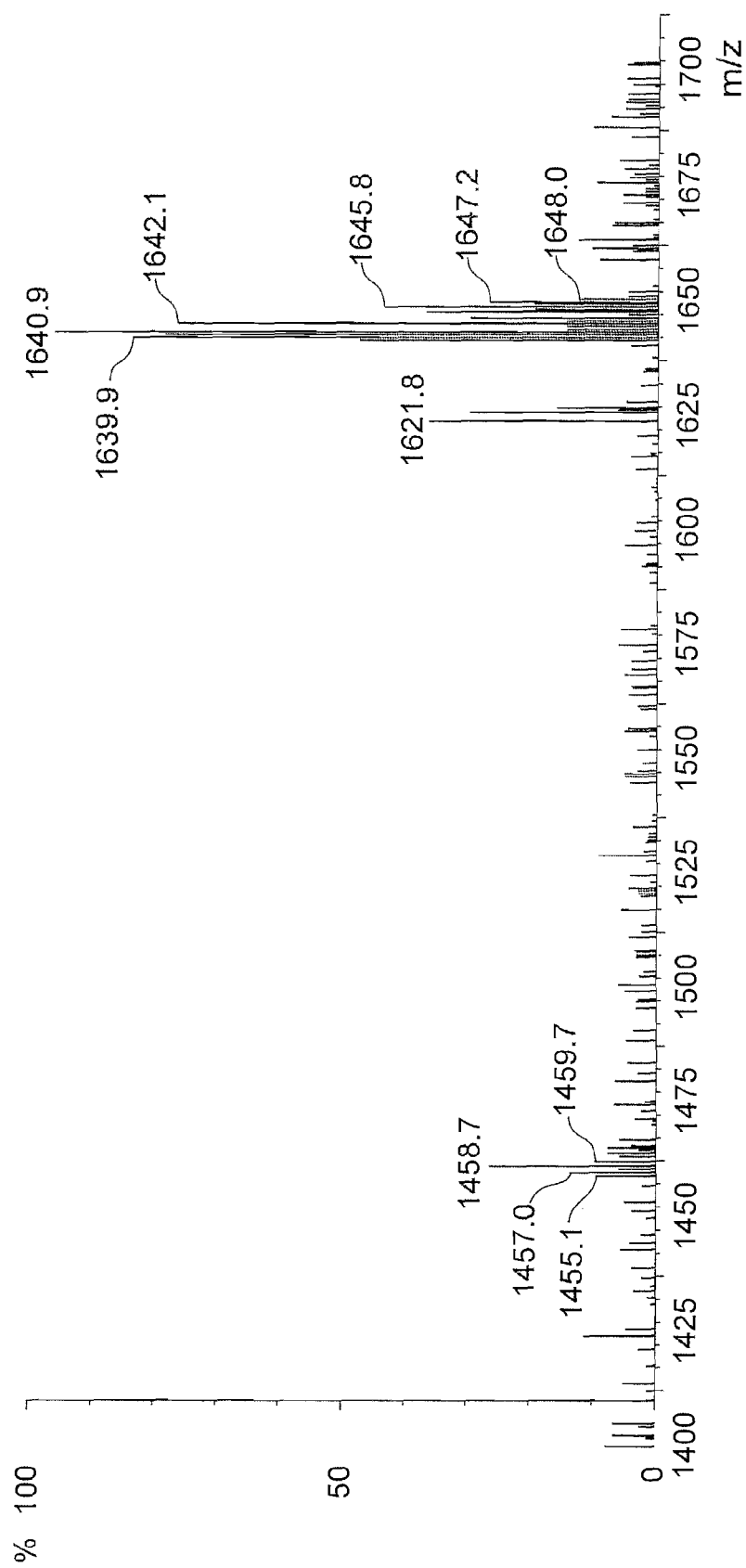
FIG. 6 shows a MS chart of TC9A.

The mixed cyclic phenol sulfide of the present invention indicated total ion chromatogram (TIC) as indicated in FIG. 1. TC4A wherein, in the formula (1), R=tert-butyl group, and m=4 indicated MS spectrum as indicated in FIG. 2 and attributes to m/z=721 (M+H), 738 (M+NH4). TC6A wherein, in the formula (1), R=tert-butyl group, and m=6 indicated MS spectrum as indicated in FIG. 3 and attributes to m/z=1081 (M+H), 1098 (M+NH4). TC8A wherein, in the formula (1), R=tert-butyl group, and m=8 indicated MS spectrum as indicated in FIG. 4 and attributes to m/z=1441 (M+H), 1458 (M+NH4). TC7A wherein, in the formula (1), R=tert-butyl group, and m=7 indicated MS spectrum as indicated in FIG. 5 and attributes to m/z=1261 (M+H), 1278 (M+NH4). TC9A wherein, in the formula (1), R=tert-butyl group, and m=9 indicated MS spectrum as indicated in FIG. 6 and attributes to m/z=1621 (M+H), 1638 (M+NH4).

The mixture obtained by the above method was purified by recrystallization from THF/chloroform. The mixed cyclic phenol sulfide of the present invention obtained by the purification was clarified as the following mixture.

|  | Peak area ratio | mol % |
| --- | --- | --- |
| m = 4 | 69.3% | 76.9 mol % |
| m = 6 | 21.1% | 17.3 mol % |
| m = 8 | 9.6% | 5.8 mol % |

EXAMPLE 2

120.2 g of 4-tert-butylphenol, 51.3 g of sulfur and 16.0 g of sodium hydroxide were poured in a 1 L four-neck flask with a mixer, a cooling tube, a thermometer and a gas-introducing tube. 360.5 g of diphenyl ether was added thereto and reacted for 1 hour at 130° C., for further 1 hour at 170° C. and then for 18 hours at 230° C., with stirring the mixture in the current of nitrogen gas and with removing water and hydrogen sulfide each of which was generated in the reaction. The reaction mixture was cooled down to room temperature, and 80 mL of an aqueous solution of 3 mol/L of a sulfuric acid was added thereto and hydrolyzed. Then, 200 mL of a mixed solvent of isopropyl alcohol/water (88/12, v/v) was added thereto, and crystals precipitated. The crystals were taken out by filtration and washed twice with 200 mL of a mixed solvent of isopropyl alcohol/water (88/12, v/v) and 240 mL of water, and further with 200 mL of a mixed solvent of isopropyl alcohol/water (88/12, v/v). The crystals were dried overnight under reduced pressure at 120° C. to obtain 113.2 g of crude crystals.

The purity of the obtained crude crystals, relative proportions thereof and the like were analyzed by a high performance liquid chromatography (hereinafter referred to as HPLC). The HPLC measurement condition is as follows: device: LC-6A by Shimadzu Corporation; column: Develosil ODS-HG-5 (inside diameter 4.6, column length 250 mm) by Nomura Chemical Co., Ltd.; column temperature: 40° C.; mobile phase: THF/acetonitrile/water/trifluoroacetic acid=450/400/150/2 (v/v/v/v); current speed: 1.0 mL/min.; filling amount: 1 μL; and concentration of a sample: 1000 ppm.

The results of the HPLC analysis clarified that the crude crystals were a mixture which comprises a cyclic quatromer wherein, in the formula (1), R is tert-butyl and m=4 indicates the peak area ratio of 96.1%; and a cyclic octamer wherein, in the formula (1), R is tert-butyl and m=8 indicates the peak area ratio of 3.6%. Converting the values to molar ratio, the cyclic quatromer is 97.7 mol % and the cyclic octamer is 2.3 mol %.

EXAMPLE 3

50 g of the crude crystals obtained in Example 2 were dispersed in 100 mL of THF and stirred overnight at room temperature. The precipitated crystals were taken out by filtration and washed with 45 mL of THF. The filtrate upon filtering the crystals and the wash solution were mixed, concentrated under reduced pressure with an evaporator, and then dried to obtain 7.4 g of brown crude crystals. 7.0 g of the brown crude crystals were dispersed in 106 mL of toluene and stirred overnight at room temperature. The precipitated crystals were taken out by filtration and washed with 10 mL of THF to obtain 2.6 g of pale yellow crystals. 1.77 g of the pale yellow crystals were dissolved by heating in 9.3 mL of THF, and then, 37 mL of chloroform was added thereto and stirred overnight with cooling. The precipitated crystals were taken out by filtration and washed with 4 mL of chloroform. The obtained crystals were dried overnight under reduced pressure at 120° C. to obtain 1.2 g of white crystals. When the obtained crystals were analyzed based on the above HPLC measurement condition, a cyclic octamer wherein, in the formula (1), R is tert-butyl and m=8 indicated the peak area ratio of 97.9%.

Figure 7:
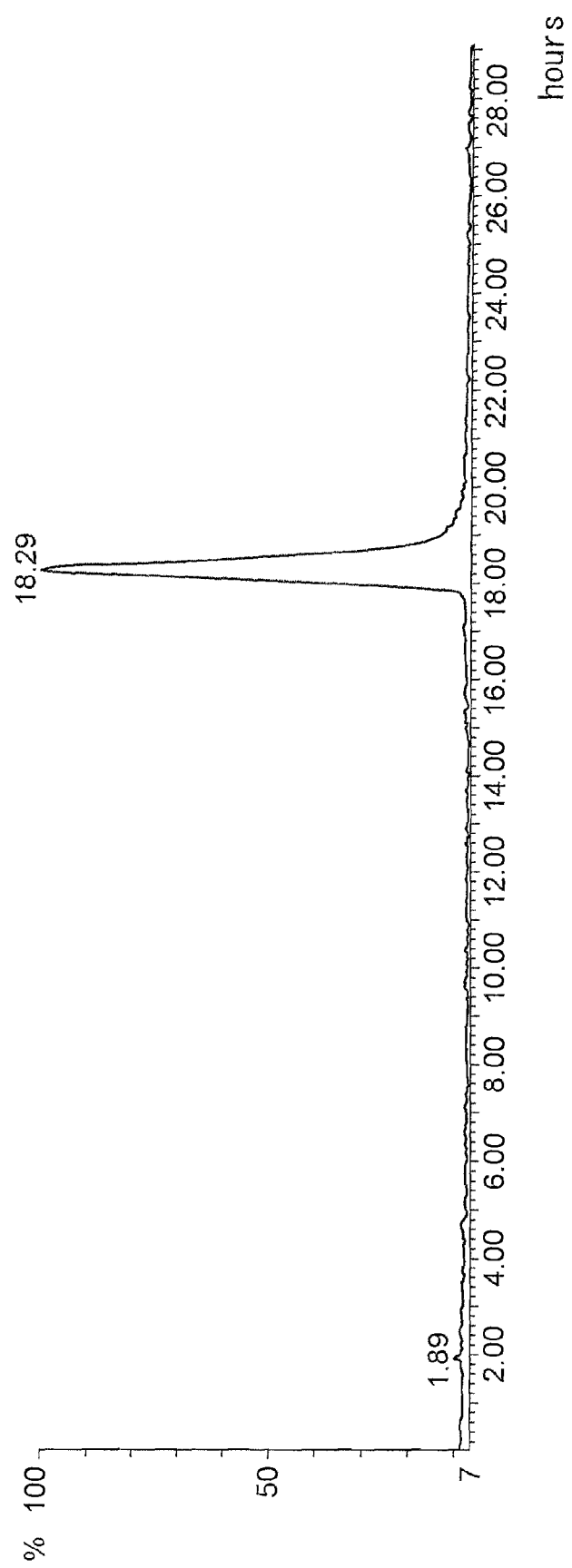
FIG. 7 shows a TIC chart of TC8A of Example 3.

The TIC chart of the obtained cyclic octamer (TC8A) is indicated in FIG. 7.

COMPARATIVE EXAMPLE 1

As a comparative compound 1, a compound disclosed in JP-A 2003-295522 (Compound A, corresponding to the compound wherein, in the formula (1), R is a tert-butyl group and m=4) was synthesized. The synthesis was conducted in accordance with the method described in JP-A 2003-295522. Namely, 113 g of 4-tert-butylphenol, 36 g of sulfur, 7.5 g of sodium hydroxide and 19 g of tetraethylene glycol dimethyl ether were poured in a 1 L four-neck flask with a mixer, a cooling tube, a thermometer and a gas-introducing tube, and gradually heated up to 230° C. in 4 hours with stirring the mixture under nitrogen atmosphere. Then, the mixture was further stirred for 2 hours. During the reaction, water and hydrogen sulfide each of which was generated in the reaction were removed. The reaction mixture was cooled down to room temperature and dissolved in diethyl ether added thereto. Then, the mixture was hydrolyzed with an aqueous solution of 0.5 mol/L of a sulfuric acid. The isolated diethyl ether layer was washed with water and dried with magnesium sulfate. The reaction mixture obtained after removing diethyl ether was further separated with a silica gel column chromatography (hexane/chloroform) to obtain a crude product. Then, the product was purified by recrystallization from chloroform/acetone to obtain 51 g of transparent colorless crystals.

Figure 8:
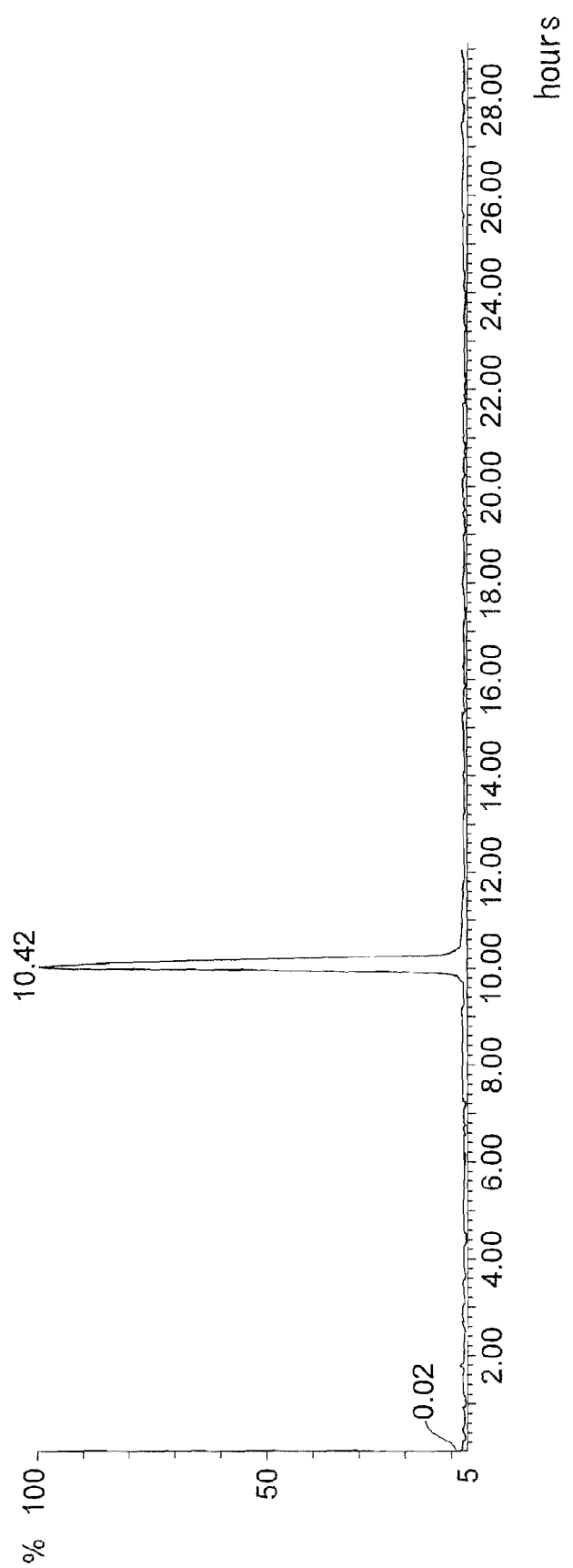
FIG. 8 shows a TIC chart of the cyclic phenol sulfide of Comparative Example 1.

The TIC chart of the obtained cyclic phenol sulfide is indicated in FIG. 8.

COMPARATIVE EXAMPLE 2

As a comparative compound 2, a compound disclosed in JP-A 2003-295522 (Compound E, see the following figure) was synthesized. The synthesis was conducted in accordance with the method described in JP-A 2003-295522. Namely, 20 g of the comparative compound 1, 1 L of acetone, 24 g of $K_2CO_3$ and 260 mL of bromoacetic acid ethyl were poured respectively in a 2 L four-neck flask with a mixer, a cooling tube and a thermometer, and heated to reflux for 6 hours under nitrogen atmosphere. After cooling, $K_2CO_3$ was filtered, acetone was removed and bromoacetic acid ethyl was removed by being dried under reduced pressure. Thus obtained reaction mixture was purified with a column chromatography (carrier:silica gel; hexane/ethyl acetate) and recrystallized (ethanol) to obtain 15 g of white powdery crystals.

Figure 9:
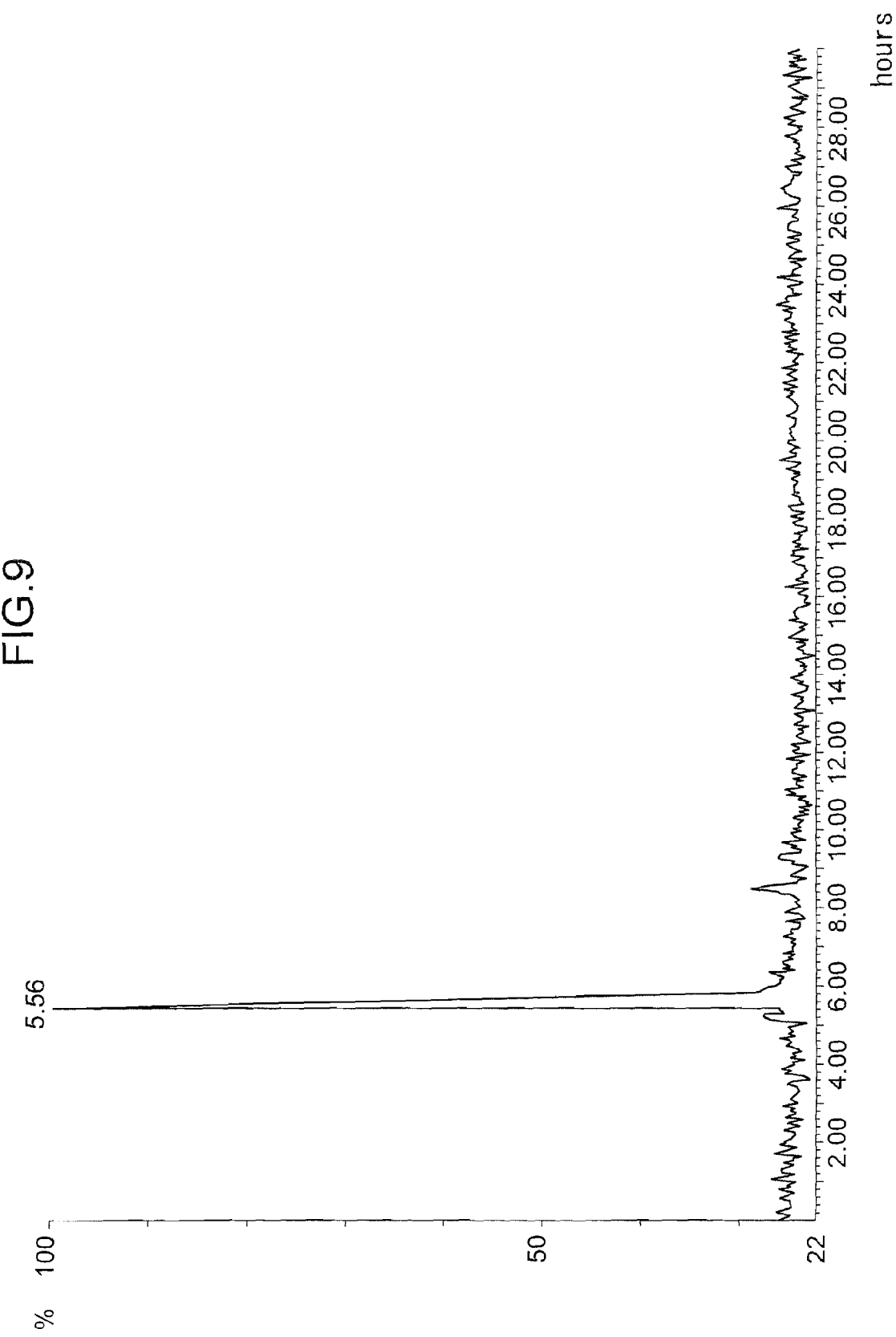
FIG. 9 shows a TIC chart of the cyclic phenol sulfide of Comparative Example 2.
Figure 10:
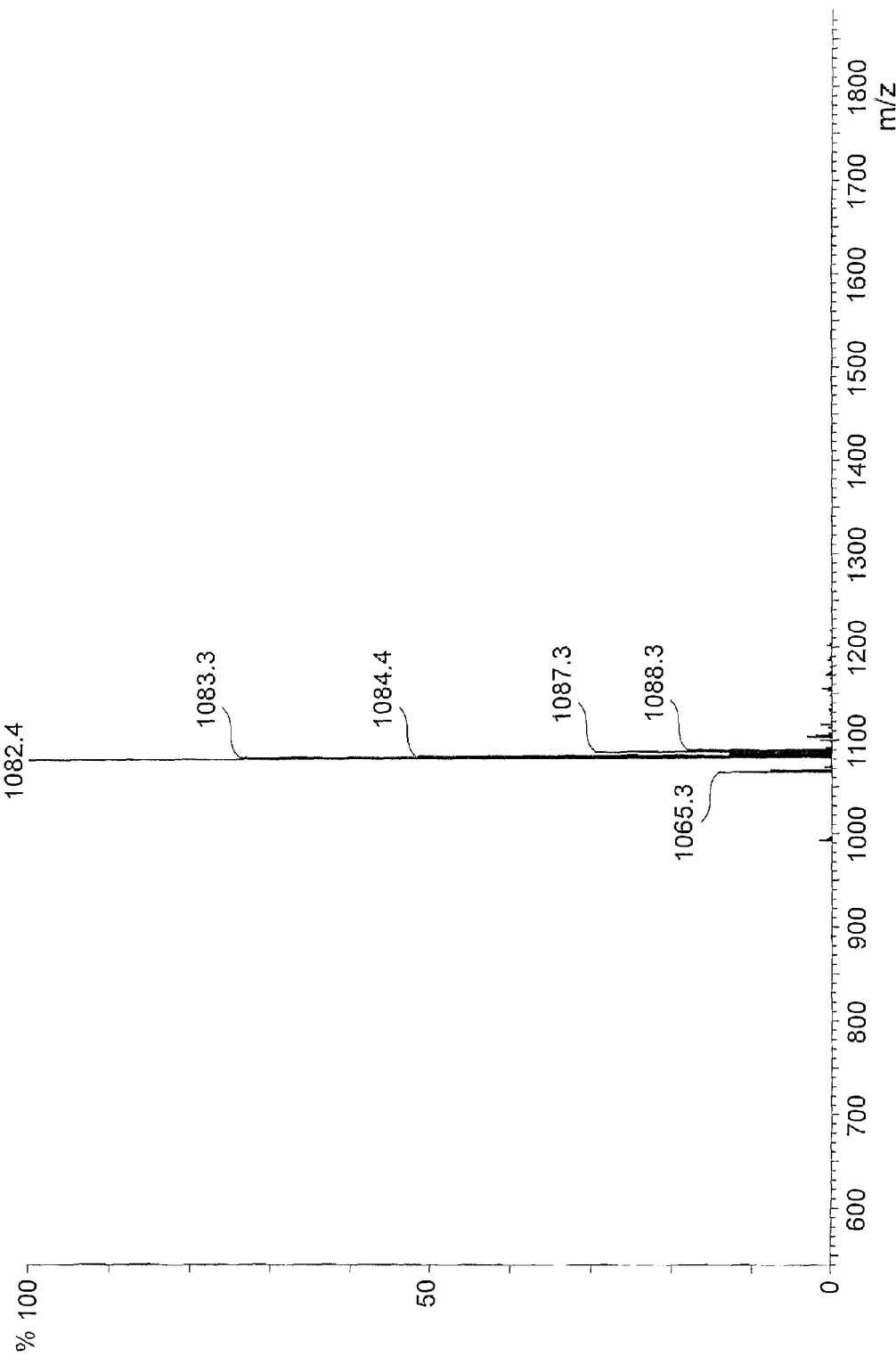
FIG. 10 shows a MS chart of the cyclic phenol sulfide of Comparative Example 2.

Each of the TIC chart and the MS chart of the obtained cyclic phenol sulfide is indicated in FIG. 9 and FIG. 10, respectively.

(Comparative Compound 2)

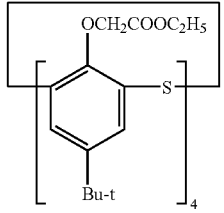

EXAMPLE 4

94 parts by weight of a styrene-acrylic acid ester copolymer resin (CPR-100 by Mitsui Chemicals, Inc.), 1 part by weight of the mixed cyclic phenol sulfide synthesized in Example 1 or 3, and 5 parts by weight of carbon black (MA-100 by Mitsubishi Chemical Corporation) were mixed by melting at 110° C. with a heat mixing machine. Then, the cooled down mixture was roughly crushed with a hammer mill. Then, the mixture was finely crushed with a jet mill and classified to obtain a black toner having the average particle diameter on the volumetric basis of 10±0.5 µm. 4 parts by weight of the toner and 100 parts by weight of a non-coat ferrite carrier (F-150 by Powdertech Co., Ltd.) were mixed and shaken to charge the toner negatively. Then, the mixture was measured with a blow-off powder charge amount measurement device at 25° C. and at 50% humidity. The result is shown in Table 1.

COMPARATIVE EXAMPLE 3

For comparison, a toner was prepared by the same condition as that of Example 4 except that the mixed cyclic phenol sulfide synthesized in Example 1 was replaced with the compound synthesized in Comparative Example 1 (Compound A), and the charge amount thereof was measured. The result is shown in Table 1.

COMPARATIVE EXAMPLE 4

For comparison, a toner was prepared by the same condition as that of Example 4 except that the mixed cyclic phenol sulfide synthesized in Example 1 was replaced with the compound synthesized in Comparative Example 2 (Compound E), and the charge amount thereof was measured. The result is shown in Table 1.

EXAMPLE 5

94 parts by weight of a styrene-acrylic acid ester copolymer resin (CPR-100 by Mitsui Chemicals, Inc.), 1 part by weight of the mixed cyclic phenol sulfide synthesized in Example 1 or 3, and 5 parts by weight of carbon black (MA-100 by Mitsubishi Chemical Corporation) were mixed by melting at 110° C. with a heat mixing machine. Then, the cooled down mixture was roughly crushed with a hammer mill. Then, the mixture was finely crushed with a jet mill and classified to obtain a black toner having the average particle diameter on the volumetric basis of 10±0.5 µm. 4 parts by weight of the toner and 100 parts by weight of a silicon-coated ferrite carrier (F96-150 by Powdertech Co., Ltd.) were mixed and shaken to charge the toner negatively. Then, the mixture was measured with a blow-off powder charge amount measurement device at 25° C. and at 50% humidity. The result is shown in Table 1.

COMPARATIVE EXAMPLE 5

For comparison, a toner was prepared by the same condition as that of Example 5 except that the mixed cyclic phenol sulfide synthesized in Example 1 was replaced with the compound synthesized in Comparative Example 1 (Compound A), and the charge amount thereof was measured. The result is shown in Table 1.

COMPARATIVE EXAMPLE 6

For comparison, a toner was prepared by the same condition as that of Example 5 except that the mixed cyclic phenol sulfide synthesized in Example 1 was replaced with the compound synthesized in Comparative Example 2 (Compound E), and the charge amount thereof was measured. The result is shown in Table 1.

TABLE 1

| Used compound | Carrier F-150 charge amount (µc/g) | Carrier F96-150 charge amount (µc/g) |
|---|---|---|
| Sulfide synthesized in Exam. 1 | −55.31 | −22.29 |
| Sulfide synthesized in Exam. 3 | −57.91 | −23.14 |
| Compound A synthesized in Comp. Exam. 1 | −19.72 | −14.83 |
| Compound E synthesized in Comp. Exam. 2 | −5.05 | −0.13 |

The mixed cyclic phenol sulfides synthesized in Examples 1 and 3 showed excellent charging performance as compared with the compounds synthesized in Comparative Examples 1 and 2 (Compounds A and E).

Namely, it was clarified that the mixed cyclic phenol sulfides of the present invention have more excellent charging performance than each single cyclic phenol sulfide; that charge control agents containing said mixed compound have excellent charge providing effect; and that negative electric toners containing said charge control agent have high charging performance.

The mixed cyclic phenol sulfides of the present invention have excellent charging performance, and charge control agents containing said mixed compound clearly have higher charging performance than conventional charge control agents. Further, since they are completely colorless, they are useful for color toners. Besides, they do not comprise heavy metals such as chromium compounds, which are concern for the environmental problem, and thus, it is possible to provide extremely useful toners.

What is claimed is:

1. A toner which comprises a mixed cyclic phenol sulfide, a coloring agent and a binder resin, the mixed cyclic phenol sulfide being a mixture of cyclic phenol sulfide wherein m is 8 and cyclic phenol sulfide wherein m is an integer other than 8, the cyclic phenol sulfide being represented by the following formula (1):

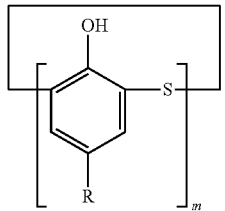

(1)

wherein R is a straight or branched alkyl group having 1 to 6 carbon atoms, and m is an integer from 4 to 9, wherein in the mixture, the content of the cyclic phenol sulfide wherein m is 8 is 1 mol % or more.

2. The toner according to claim 1, wherein, in the mixture, the content of the cyclic phenol sulfide wherein m is 8 is 1.5 mol % to 25 mol %; and the content of the cyclic phenol sulfide wherein m is 4 is 75 mol % to 98 mol %.

3. A toner which comprises a cyclic phenol sulfide, a coloring agent and a binder resin, the cyclic phenol sulfide being represented by the following formula (1):

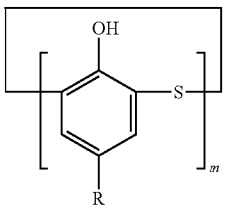

(1)

wherein R is a straight or branched alkyl group having 1 to 6 carbon atoms, and m is 8.

* * * * *